(12) United States Patent
Li et al.

(10) Patent No.: US 7,556,825 B2
(45) Date of Patent: *Jul. 7, 2009

(54) METHOD FOR PROMOTING HAIR GROWTH

(75) Inventors: Lingna Li, San Diego, CA (US); Valeryi Lishko, Shaker Heights, OH (US)

(73) Assignee: Anticancer, Inc., San Diego, CA (US)

( * ) Notice: Subject to any disclaimer, the term of this patent is extended or adjusted under 35 U.S.C. 154(b) by 552 days.

This patent is subject to a terminal disclaimer.

(21) Appl. No.: 10/840,908

(22) Filed: May 7, 2004

(65) Prior Publication Data

US 2004/0205910 A1 Oct. 21, 2004

Related U.S. Application Data

(60) Continuation of application No. 08/859,051, filed on May 20, 1997, now Pat. No. 6,733,776, which is a division of application No. 08/486,520, filed on Jun. 7, 1995, now Pat. No. 5,753,263, which is a continuation-in-part of application No. PCT/US94/03634, filed on Apr. 1, 1994, which is a continuation-in-part of application No. 08/181,471, filed on Jan. 13, 1994, now Pat. No. 5,641,508, which is a continuation-in-part of application No. 08/041,553, filed on Apr. 2, 1993, now abandoned.

(51) Int. Cl.
*A61K 9/127* (2006.01)
*A61K 7/13* (2006.01)

(52) U.S. Cl. ............... 424/450; 424/401; 424/70.1; 424/70.6

(58) Field of Classification Search ............ 424/450, 424/401, 70.1, 70.6
See application file for complete search history.

(56) References Cited

U.S. PATENT DOCUMENTS

| 3,993,436 A | 11/1976 | Fujinuma ............... 424/70.1 |
| 4,241,046 A | 12/1980 | Papahadjopoulos et al. . 424/420 |
| 4,394,448 A | 7/1983 | Szoka et al. ............ 435/172.3 |
| 4,755,388 A | 7/1988 | Heath et al. ............. 424/450 |

(Continued)

FOREIGN PATENT DOCUMENTS

DE 4113346 10/1992

(Continued)

OTHER PUBLICATIONS

Gregoriadis, Trends in Biotechnology (1985) 3(9):235-241.

(Continued)

*Primary Examiner*—Gollamudi S Kishore
(74) *Attorney, Agent, or Firm*—Morrison & Foerster LLP

(57) ABSTRACT

The present invention describes a method for targeted and specific delivery of beneficial compounds, including hair dyes, melanin, proteins, and nucleic acids for gene therapy, to hair follicle cells using liposomes encapsulating the beneficial compound. Particularly preferred methods describe delivery of hair dyes, melanin or tyrosinase to the hair follicle for the purpose of improving hair color or condition, the delivery of compounds which prevent alopecia or stimulate hair growth, either by encapsulating a compound in liposomes, or by encapsulating a nucleic acid capable of expressing a protein in liposomes. Also described are liposome compositions for practicing the methods.

3 Claims, 20 Drawing Sheets

U.S. PATENT DOCUMENTS

| | | | | |
|---|---|---|---|---|
| 4,919,664 | A | 4/1990 | Oliver et al. | 128/898 |
| 4,925,661 | A | 5/1990 | Huang | 424/178.1 |
| 4,954,345 | A | 9/1990 | Muller | 424/450 |
| 4,957,735 | A | 9/1990 | Huang | 424/178.1 |
| 5,006,331 | A | 4/1991 | Gaskin | 424/70.1 |
| 5,043,164 | A | 8/1991 | Huang et al. | 424/450 |
| 5,064,655 | A | 11/1991 | Uster et al. | 435/193 |
| 5,077,211 | A | 12/1991 | Yarosh | 435/193 |
| 5,130,142 | A | 7/1992 | Wong | 424/574 |
| 5,182,269 | A | 1/1993 | Gazzani et al. | 514/44 |
| 5,190,762 | A | 3/1993 | Yarosh | 424/193 |
| 5,210,076 | A | 5/1993 | Berliner et al. | 514/21 |
| 5,223,263 | A | 6/1993 | Hostetler et al. | 424/450 |
| 5,286,979 | A | 2/1994 | Berliner | 250/515.1 |
| 5,290,562 | A | 3/1994 | Maybeck et al. | 424/450 |
| 5,302,389 | A | 4/1994 | Kripke | 424/94.6 |
| 5,384,126 | A | 1/1995 | Bonte | 424/450 |
| 5,443,839 | A | 8/1995 | Meybeck | 424/450 |
| 5,470,579 | A | 11/1995 | Bonte et al. | 424/450 |
| 5,556,956 | A | 9/1996 | Roy | 536/24.1 |
| 5,618,798 | A | 4/1997 | Bar-Shalom et al. | 514/53 |
| 5,641,508 | A * | 6/1997 | Li et al. | 424/450 |
| 5,641,509 | A | 6/1997 | Gross | 424/450 |
| 5,723,146 | A | 3/1998 | Rossling | 424/450 |
| 5,753,263 | A * | 5/1998 | Lishko et al. | 424/450 |
| 5,914,126 | A * | 6/1999 | Li et al. | 424/450 |
| 6,224,901 | B1 * | 5/2001 | Li et al. | 424/450 |
| 6,261,596 | B1 * | 7/2001 | Li et al. | 424/450 |
| 6,733,776 | B1 * | 5/2004 | Li et al. | 424/450 |
| 6,844,326 | B2 * | 1/2005 | Li | 514/44 |

FOREIGN PATENT DOCUMENTS

| | | |
|---|---|---|
| EP | 369105 | 5/1990 |
| FR | 2648132 | 6/1989 |
| FR | 2648132 | 12/1990 |
| FR | 2669225 | 5/1992 |
| WO | WO 88/07362 | 10/1988 |
| WO | WO 90/00389 | 1/1990 |
| WO | WO 91/07945 | 6/1991 |
| WO | WO 92/00057 | 1/1992 |
| WO | 94/03634 | 4/1994 |
| WO | WO 94/03634 | 4/1994 |

OTHER PUBLICATIONS

Hoffman et al., FEBS Letters (Sep. 1978) 98(2):365-368.
Hoffman et al., In Vitro Cell. Dev. Biol. (Mar. 1993) 29A:192-194.
Jiminez et al., Cancer Invest. (1992) 10:271-276.
Juhano, Antisense Res. and Development (1992) 2:165-176.
Li et al., In Vitro Cell. Dev. Biol. (1992) 28A:679-681.
Li et al., In Vitro Cell. Dev. Biol. (1993) 29A:192-194.
Lieb et al., Journal of Investigative Dermatology (Jul. 1992) 99(1):108-113.
Maigach et al., Arch. Environ. Health 23 (Sep. 1971):208-211.
Mezei, Life Sciences (1980) 26:1473-1477.
Miranda et al., Biochim. Biophys. Acta. (1988) 966:276-286.
Plessis, Antiviral Res. (1992) 18:259-265.
Rowe, Prostate (1984) 5:346-347.
Schmidt, K.H. ed., Liposomes as drug carriers, Stuttgart: George Thieme Verlag (1986).
Smitz et al., Cancer Research (1992) 52(23):6638-6645.
Stuhne-Sekalec, J. Microencapsulation (1989) 6(2):177-182.

* cited by examiner

D-282

D-378

D-383

D-3886

D-3897

D-3899

Liposome-melanin hair-follicle-targeted hair coloring
Liposome-melanin
Naked melanin
FIGURE 12A
FIGURE 12B Liposome-melanin hair-follicle-targeted hair coloring
Liposome-melanin                Naked melanin
FIGURE 13A                        FIGURE 13B

METHOD FOR PROMOTING HAIR GROWTH

This application is a continuation of U.S. Ser. No. 08/859,051, filed May 20, 1997, which is a divisional of U.S. Ser. No. 08/486,520, filed Jun. 7, 1995, which is a continuation-in-part of International Application No. PCT/US94/03634, filed Apr. 1, 1994, designating the United States, which is a continuation-in-part of U.S. Ser. No. 08/181,471, filed Jan. 13, 1994, which is a continuation-in-part of U.S. Ser. No. 08/041,553, filed Apr. 2, 1993, all of which are incorporated by reference (including drawings).

TECHNICAL FIELD OF THE INVENTION

This invention relates to methods for specifically delivering therapeutic or other beneficial compounds to hair follicles to improve hair growing from the follicles. These beneficial compounds include, but are not limited to, hair growth stimulators, hair growth inhibitors, compounds used to prevent alopecia, compounds used to restore natural hair pigment, and compounds used to modify the color of hair.

BACKGROUND OF THE INVENTION

There has been a long-felt need for methods of directly influencing hair growth, color and appearance, especially for treatment of alopecia in humans.

Surgical transplantation of small, discrete, skin areas having viable follicles to areas having inactive follicles is expensive, labor-intensive and relatively short-lasting. Also, as described by R. F. Oliver et al. in U.S. Pat. No. 4,919,664, follicular dermal cells can be inserted into a skin incision, resulting in hair growth along the incision. However, this is a complex technique that does nothing to stimulate existing follicles.

Treatment of the hair and skin with various creams or lotions with biologically active ingredients to improve hair growth and other conditions has generally low efficiency. A wide variety of externally applied agents are available for application to the hair to improve body, flexibility, curl, etc. These have limited and only short term usefulness. Coloring hair with various dyes requires frequent repetitions and is not always natural in appearance.

The use of biologically active compounds that are hair growth stimulators or advantageously change other hair characteristics, such as color, would seem to be a more natural and attractive approach, especially at the stage where hair-follicle cells still exist but hair growth, for unknown reasons, is adversely affected. Attempts to follow this approach have been ineffective, possibly because of the inability of stimulators to penetrate the cellular membrane of hair follicle cells and to enter into the cells where their action is needed.

In the treatment of skin with various absorbable lotions and the like it has long been known that absorption is generally greater in skin areas of higher follicular density. See, for example, Maigach et al, *Arch. Environ. Health,* 23:208-211 (1971). The absorbed materials, however, were entirely different from liposomes. It was not appreciated prior to the present invention that liposomes could be used to direct beneficial compositions preferentially to hair follicles.

Liposomes, which are artificial phospholipid vesicles, have been successfully used for delivery of different low-molecular-weight water-soluble and oil-soluble compounds into different cells. See, for example, G. Gregoriadis, *Trends in Biotechnology,* 3:235-241 (1985) and K. H. Schmidt, ed., Liposomes as drug carriers, Stuttgart: George Thieme Verlag (1986).

Liposomes are typically formed by mixing dry phospholipids with aqueous solutions giving rise to bilayers of phospholipid molecules which arrange themselves spontaneously to form close multilayered spherules. As they form, the liposomes entrap liquid and any soluble solutes that are present. A large number of substances that do not interfere with the formation of the liposomes can be incorporated, regardless of solubility, electrical charge, size and other structural characteristics. These characteristics may, however, have adverse affects in some environments limiting the use of liposomes.

Liposomes containing antibody molecules attached for specific targeting have been described for delivery of encapsulated material to targeted cells containing an antigen immunoreactive with the attached antibody, and are referred to as immunoliposomes. See, for example, U.S. Pat. Nos. 4,755,388, 4,925,661 and 4,957,735 for descriptions of immunoliposomes. In addition, liposome compositions have been described that contain protein which are administered to mammalian skin and shown to penetrate in skin keratinocytes. See, U.S. Pat. No. 5,190,762. Furthermore, DNA-liposome compositions have also been described, but were not shown to selectively deliver the nucleic acid contents to hair follicles through topical administration. See, U.S. Pat. Nos. 5,077,211 and 5,223,263, and Hoffman et al., *FEBS Letts.,* 93:365-368 (1978).

Although various targeting mechanisms have been attempted to increase the specificity of delivery via liposomes, delivery of the encapsulated material into a targeted cell or tissue may not necessarily follow.

Specific tissue delivery is particularly important where the agent being delivered may have a deleterious effect to tissues adjacent to the targeted tissue of interest upon administration of the agent. For example, the agent may produce effects which are acceptable in the hair follicle, but not desired in the adjacent skin tissue. For example, delivery of melanin is desirable for hair pigmentation, but may or may not be desirable for general skin pigmentation, and therefore general delivery to all surface skin cells may be undesirable, requiring follicle cell specificity. Similarly, gene replacement therapy for expressing melanin or tyrosinase may be undesirable in skin cells, but is a desirable result for hair pigmentation.

Transdermal drug delivery provides additional problems where the drug being delivered is destined for the circulation rather than cells of the dermis. Methods for transdermal drug delivery which minimize adsorption into cells of the skin and simultaneously increase transport to the circulation are desirable in certain instances. However, in instances where delivery is directed solely to the hair follicle, it is desirable that there is minimum adsorption into the skin and minimum transport of the compound into the systemic circulation where the administered compound can exert undesirable side effects.

A small molecule dye, carboxyfluorescein has been found to be delivered to the pilosebaceous units of hamster ear membrane when incorporated in a particular liposomal formulation, as described in a very recent paper by Lieb et al, *The Journal of Investigative Dermatology,* 99:108-113 (1992). Similarly, Li et al., *In Vitro Cell. Dev. Biol.,* 28A:679-681 (1992), have recently described liposome-mediated delivery of the small molecule dye calcein to hair follicles in an in vitro intact skin histoculture system.

The prior research, however, does not describe methods of specifically and selectively (preferentially) targeting hair follicles using liposomes containing large molecule agents such as proteins or nucleic acids, lipophobic agents that cannot transfer across lipid barriers or lipophilic agents which are capable of undesirable side effects on tissues other that hair follicles.

Furthermore, there have not been any descriptions of methods for accurately testing in vitro the extent to which particular compounds are delivered to hair follicle cells, the effectiveness of the compounds delivered, or liposome formulations for optimizing selectivity of targeting to hair follicles.

Thus, there is a continuing need for improved methods of selectively delivering specific beneficial compounds to hair follicles, and for measuring effectiveness of the delivery.

SUMMARY OF THE INVENTION

It has now been discovered that liposomes can selectively target the hair follicle with potentially beneficial compounds. The invention describes the unexpected results obtained by the inventors that liposomes selectively deliver compounds to the hair follicle thus enabling the compounds to cross the stratum corneum and be delivered to the cells in the hair follicle without delivery of the compounds to the surrounding skin cells.

The present invention provides compositions and methods which are useful for the specific delivery of beneficial compounds to hair follicle cells to, for example, improve hair color or condition, prevent alopecia, or to stimulate hair growth.

This invention describes methods for preparing liposomes, incorporating beneficial compounds into the liposomes either during formation of the liposomes or thereafter, and applying the liposomes to the skin areas requiring treatment in patients requiring such beneficial treatment. According to the present methods, liposomes preferentially deliver the beneficial compounds to the hair follicles where the compounds enter into the follicle cells. By virtue of the selectivity of the liposome-mediated delivery method, the administered compounds are not delivered substantially to the dermis or internally to the circulation, thereby minimizing undesirable side effects that the administered compound might exert on such dermis tissue or systemically in the circulation.

Thus, the invention provides a method of delivering beneficial compounds to the hair follicle and thus to the cells in the hair follicle. The invention provides a method of delivering any compound to the hair follicle by the use of liposomes. Although particular liposome compositions are specifically used as examples herein, the invention provides for the use of potentially any liposome to deliver the beneficial compound. Those of ordinary skill in the art will readily appreciate that any liposome may be used and that the invention is not limited to the particular types of liposomes described herein.

Thus, in a first aspect, the invention provides a method of directly and selectively delivering a beneficial compound to hair follicles of a mammal comprising the step of applying a liposome composition topically to skin areas of a mammal having a plurality of hair follicles, wherein the liposome composition comprises a liposome containing an effective amount of at least one selected beneficial compound, the liposome is capable of selectively delivering the beneficial compound to the hair follicle and the beneficial compound is preferentially transmitted to the hair follicle and enters into the hair follicle without substantially entering into the cells external to the hair follicle.

By "substantially" is meant that the compound is not appreciably delivered to the surrounding skin cells. Generally, approximately 5-20% of the compound in the liposome composition that is topically applied enters into the cells of the treated skin tissue. More commonly, 10% of the liposome composition topically applied enters the cells of the treated skin tissue. By "substantially" is meant that not more than 10% of the compound that enters the cells is delivered to the cells external to the hair follicle. More preferably, not more than 1% of the compound that enters the cells is delivered to the cells external to the hair follicle cells. In especially preferred embodiments, not more than 0.1-0.5%, preferably 0.1%, of the compound that enters the cells is delivered to cells external to the hair follicle.

Thus, one advantage of the invention is that beneficial compounds may be directly and selectively delivered to cells in the hair follicle without entering into other cells, such as other cells in the skin or the blood stream.

By "directly and selectively" is meant that the invention delivers the compound preferentially to the hair follicle and does not substantially deliver the compound to the cells surrounding the hair follicle that are not hair follicle cells or to the systemic circulatory system.

The present invention thus yields the surprising result that beneficial compositions may be directly and selectively delivered to hair follicles without transmission to the cells external to the hair follicles. The mechanism by which this selective transmission may take place may be, for example, but not by way of limitation, due to an attraction of the liposome compositions to the oil secreted by the sebaceous glands associated with the hair follicles.

Typically, the present methods are practiced on the skin of a mammal requiring treatment according to the present methods, such as a human. Thus, the methods can be practiced in vivo.

In order to determine the effectiveness of the hair follicle-specific treatment method of the present invention, an in vitro method of testing particular liposome agents has been developed, utilizing novel histoculturing techniques.

As mentioned above, it is known that a number of compounds, typically dyes and the like, when applied to the skin are more rapidly absorbed in heavily follicularized areas. However, many macromolecular or lipophobic substances cannot cross the plasma membrane or other lipid barriers into the follicle and follicle cells. In the present invention, it has been discovered that when incorporated into liposomes, those macromolecular compounds are successfully transported into the follicle cells, and furthermore can be selectively transferred across the stratum corneum into the follicle without entry to the circulation or the adjacent skin tissue, which has great potential efficacy as well as safety advantages.

Thus, the invention describes in one embodiment a liposome composition comprising a liposome containing an effective amount of a beneficial compound. The liposome utilized in the liposome composition is capable of selectively delivering the beneficial compound to hair follicles as described further herein. The beneficial compound to be administered can be a macromolecule or lipophobic molecule that is not capable of passage through the stratum corneum or cell membrane and requires the liposome-mediated delivery system to selectively and preferentially enter the hair follicle, or is a lipophilic molecule having undesirable effects on cells external to the hair follicles, and requires the selectivity of the liposome-mediated delivery system to preferentially deliver the lipophilic molecule to the hair follicle.

The liposome compositions can be utilized for a variety of applications, as described herein, and therefore may contain any of a variety of beneficial compounds, including hair color-restoring or modifying agents such as melanin, hair dye, tyrosinase, or a nucleic acid which is capable of expressing human tyrosinase, hair growth stimulating or hair fortifying agents, agents which inhibit sensitivity to chemo-therapeutics, other agents which prevent all forms of alopecia and the like beneficial compounds. These beneficial compounds may therefore be, for example, but are not limited to, proteins, peptides, nucleic acids, polymers, macromolecules, or dyes.

A liposome composition can comprise any of a variety of liposomes designed to selectively target hair follicles, including pH-sensitive liposomes, liposomes comprising a phospholipid selected from the group consisting of phosphatidylcholine (PC), egg phosphatidylcholine (EPC), dioleoylphosphatidylcholine (DOPC), dipalmitoylphosphatidyl choline (DPPC), phosphatidylethanolamine (PE), dioleoylphosphatidylethanolamine (DOPE) and cholesterol, liposomes further comprising a cationic phospholipid selected from the group consisting of D282, D378, D383, D3886, D3897 and D3899, (obtainable from Molecular Probes Catalog, Eugene, Oreg.) and the like formulations.

The invention also describes a method for restoring hair color to the hair of a mammal, comprising applying a therapeutically effective amount of a liposome composition to a skin area on said mammal having a plurality of hair follicles, where the liposome composition of the present invention comprises a liposome containing an effective amount of at least one selected hair color-restoring agent. Preferred hair color-restoring agents include melanin, hair dye, tyrosinase, and a nucleic acid capable of expressing human tyrosinase in hair follicle cells, more preferably, the nucleic acid encodes human tyrosinase including the amino acid residue sequence characteristics of the tyrosinase protein sequence SEQ ID NO 1.

The invention further describes a method of directly and selectively delivering a beneficial compound to hair follicles of a mammal comprising the step of applying a liposome composition of this invention topically to skin areas of a mammal having a plurality of hair follicles, wherein the liposome composition comprises a liposome containing an effective amount of at least one selected beneficial compound and wherein the beneficial compound is a macromolecule, a lipophobic molecule or a lipophilic molecule having undesirable effects on cells external to said hair follicles. The liposome composition may be applied to the skin area of a mammal having a plurality of hair follicles either in vivo, or in vitro, using explanted skin tissue. The explanted skin tissue may be grown, for example, as described herein, in skin histoculture. In preferred embodiments, the beneficial compound is a hair color-restoring agent such as melanin, hair dye, or tyrosinase. In related embodiments, the beneficial compound is a hair growth stimulator such as cyclosporin-A, or related compounds, finesteride, or an antisense nucleic acid molecule that would block a gene conferring a negative effect to the hair. Techniques of designing antisense molecules are well known to those of ordinary skill in the art. Hair growth stimulating compounds may have undesirable side effects when delivered systemically, one advantage of the present invention provides compounds for and a method of directly and selectively delivering the compounds to the hair follicle cells without substantially delivering the compound to the bloodstream, thus avoiding such undesirable side effects. In another related embodiment, the beneficial compound is a nucleic acid capable of expressing an effective amount of a replacement therapy protein. Particularly preferred are nucleic acid molecules capable of expressing tyrosinase or hair-growth stimulating proteins or the multi-drug resistance proteins conferring resistance to chemotherapy-induced alopecia.

In other embodiments, the invention contemplates the use of the present liposome compositions according to the present methods for inhibiting chemotherapy-induced alopecia. The liposome compositions contain compounds which reduce in the hair follicle the toxicity of the chemotherapy treatment.

BRIEF DESCRIPTION OF THE DRAWINGS

Details of the invention, and of certain preferred embodiments thereof, will be further understood upon reference to the drawings, wherein:

FIGS. 5A-5D contain light microscopy images (magnification 125×, FIGS. 5A and 5C; magnification 250×, FIGS. 5B and 5D) of sections of skin histoculture prepared as described in Example 4b, in which FIGS. 5A and 5B illustrate results using liposome-entrapped plasmid (pM-MuLV-SV-Lac-Z) capable of expressing Lac-Z, and FIGS. 5C and 5D illustrate results using naked plasmid. The arrows indicate uniform distributions of blue (dark) spots in the hair follicles and shafts indicating active gene transfer to the hair follicles;

FIGS. 6A-6C contain fluorescent light microscopy images (magnification 150×) of sections of mouse skin samples prepared by treatment of mouse skin in vivo as described in Example 5, in which FIGS. 6A and 6B illustrate results using liposome-entrapped calcein and FIG. 6C illustrates results using naked calcein. The arrows indicate fluorescence in the hair shafts indicating active transfer of calcein to the hair follicles;

FIGS. 7A-7C contain light microscopy images (magnification 500×) of sections of mouse skin samples prepared by treatment of mouse skin in vivo as described in Example 5, in which FIGS. 7A-7C illustrate results using liposome-entrapped melanin.

FIG. 11A is a light microscopy image and FIGS. 11B and 11C are histological sections of the same sample as FIG. 11A, as described in Example 2.

FIGS. 12A and 12B contain light microscopy images of mouse skin treated with melanin entrapped in liposomes (12A), and mouse skin treated with naked melanin (12B), as described in Example 2.

FIGS. 13A and 13B contain photographs of mice treated with melanin entrapped in liposomes (13A) and with naked melanin (13B), as described in Example 2.

Figure 1A:
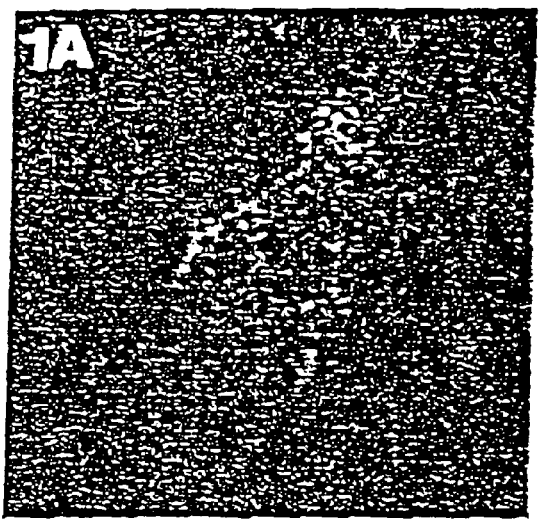
FIG. 1A is a fluorescent microscopy image (magnification 500×) of a skin histoculture treated with liposomes containing calcein as described in Example 1 showing highly preferential dye delivery into hair follicles.

The drawings are not necessarily to scale, and certain features of the invention may be exaggerated in scale and shown in schematic form in the interest of clarity and conciseness.

DETAILED DESCRIPTION OF THE INVENTION

A. Liposome-Mediated Targeted Delivery of Macromolecules and Nucleic Acids to Hair Follicles The invention relates to the administration of active compositions directly and selectively (specifically) to the cells of the hair follicle and to the hair shaft itself.

Because of the hair follicle specificity for delivery according to the present invention, the present invention provides the advantage of specifically delivering beneficial compositions to the hair follicle rather than generally to the dermis or circulation, thereby allowing the use of lower amounts of the composition to achieve the desired effect, and thereby reducing the likelihood of undesirable effects caused by the composition on the skin generally or to the general circulation.

1. Skin Histoculture Assay

In order to demonstrate that liposomes encapsulating beneficial compounds are effective at selective delivery, and to provide a means for optimizing liposome mediated delivery formulations, an in vitro assay has been developed. Basically, pieces of skin containing hair follicles are histocultured on collagen-gel-supported sponges as described by Li et al, *Proc. Natl. Acad. Sci. USA,* 88:1908-1912 1991); Li et al, *Proc. Natl. Acad. Sci. USA* 89:8764-8768, 1992; Li et al., *In Vitro Cell. Dev. Biol.* 28A:479-481, 1992; Li et al., *In Vitro Cell. Dev. Biol.* 28A:679-681, 1992; Li et al., *In Vitro Cell. Dev. Biol.* 28A:695-698, 1992; Li et al., *In Vitro Cell. Dev. Biol.* 29A:192-194, 1993; and Li et al., *In Vitro Cell. Dev. Biol.* 29A:449-450, 1993, the teachings of which are hereby incorporated by reference. The system allows the growth of hair shafts in the follicle cells for periods of at least 10-16 days, and further allows the ability to evaluate the three-dimensional appearance of the hair follicle and surrounding tissue by the use of selective dyes and stains in confocal microscopy, thereby providing a system for evaluating the effectiveness of the therapeutic reagent being applied. The use of the three-dimensional histoculture in conjunction with confocal microscopy allows the ability to follow the fine details of candidate beneficial (therapeutic) product-delivering liposome interactions with hair-follicles at the cellular and subcellular level. Therefore, the histoculture system allows the ability to optimize liposome compositions as well as determine the optimum conditions for delivery of the liposome contents into the target cell.

Typical skin histoculture preparation methods are also detailed in copending U.S. patent application of Li et al., Ser. No. 08/129,022, filed Sep. 29, 1993, and assigned to the assignee of this application, which is a continuation of Ser. No. 07/662,239, filed Feb. 28, 1992, and assigned to the assignee of this application, and in copending International Patent Application Serial No. PCT/US92/01571, filed Feb. 28, 1992, and published on Sep. 17, 1992 as International Publication No. WO92/15700 the teachings of which are all hereby incorporated by reference.

Native-state histoculturing of a skin sample having hair follicles and internal and external surfaces comprises placing the skin sample on an extracellular support matrix immersed in a medium whereby the internal surface is adjacent to the matrix and the external surface is exposed in the air above the surface of the medium and maintaining the matrix with the skin thereon under skin culturing conditions.

Potentially any skin from any animal can be used in this assay. Preferably, the animal is a mammal. Exemplary mammals are mice, rats, guinea pigs, hamsters, rabbits, marmosets, monkeys and humans. More preferably, the animal is a human.

The skin sample having dermal and epidermal layers is typically excised from an animal. Excess fat, if present, is removed. The sample of skin may be excised from a hairy animal whose skin is capable of supporting hair growth or from a hairless animal whose skin is devoid of hair, such as an athymic, nude animal. Where the skin sample is obtained from a hairy animal, the skin may be shaved or clipped prior to excision.

The skin sample is defined herein as having internal and external surfaces. The phrase "internal surface" refers to the dermally-oriented surface; i.e. the non-exposed surface of the skin as it exists in its native-state in the animal. The phrase "external surface" refers to the epidermally-oriented surface: i.e. the exposed surface of the skin as it exists in its native-state in the animal.

There is no real limitation as to the surface area of a piece of skin used in the present invention. Typically, the skin sample can range in external surface area from about 1 to about 10,000 square millimeters ($mm^2$). A preferred surface area is from about 4 to about 100 $mm^2$. A more preferred surface area is about 10 $mm^2$. The thickness of the skin is a function of the animal from which it is obtained. Where the skin sample is excised from a mouse, a preferred thickness is about 1 to 2 mm.

Skin samples are cultured on a support matrix. A support matrix of this invention provides a trabecular structure with interstices suited for capillary action to deliver aqueous nutrients from the medium to the internal surface (base) the skin as in a native state. Thus, any support having this capacity is contemplated including synthetic meshes such as nylon, borosilicate glass fiber, or polypropylene or organic meshes such as cellulose or collagen. Preferably, the support matrix is an extracellular support matrix. As used herein, the phrase "extracellular support matrix" means a solid, such as a gel or sponge, comprising one or more organic molecules or molecular aggregates, which molecules or aggregates are those produced and secreted by cells into the extracellular space and which serve, in vivo, as a support, adhesive and framework for maintaining three-dimensional tissue organization and function. Exemplary of such molecules are high-molecular weight proteins and glycoproteins such as collagen, laminin, fibronectin and the like, complex polysaccharides and the like molecules.

In a preferred embodiment, the extracellular support matrix is a collagen-containing gel. Exemplary collagen-containing gels are gelatinized pig skin such as GELFOAM™ (The Upjohn Company, Kalamazoo, Mich.) and a composition comprising laminin, collagen, proteoglycan and entactin such as MATRIGEL™ (Collaborative Research, Inc., Bedford, Mass.). GELFOAM™ is a patented product described in U.S. Pat. No. 2,465,357, the disclosure of which is incorporated herein by reference.

In another preferred embodiment, the extracellular support matrix is a homopolysaccharide sponge (Leighton, J., *J. Nat'l Cancer Instit.* 12:545-561, 1951). A preferred homopolysaccharide is cellulose. Homopolysaccharide sponges contemplated by the present invention are not limited as to weave or net size.

In still another preferred embodiment, the extracellular support matrix comprises a combination of a collagen-containing gel and a homopolysaccharide sponge. Preferably, such a combination comprises a top layer of a collagen-containing gel and a bottom layer of a homopolysaccharide sponge. The collagen-containing gel is preferably gelatinized pig skin and the homopolysaccharide is preferably cellulose. In a particularly preferred embodiment, the support matrix comprises a combination of a top layer of GELFOAM™ and a bottom layer of a cellulose sponge, which matrix has been shown to be most effective in maintaining normal hair growth of histocultured skin.

There are no set ratios of skin sample size to size of the extracellular support matrix. The matrix can be anywhere from a diameter which is sufficient to support the skin sample to being greater in size and substantially overlapping the skin sample. Multiple samples can be placed on the same matrix so long as the skin samples are not actually touching. A preferred distance between skin samples is about 1 to 2 mm.

The skin sample is placed on the matrix such that the internal surface of the skin is adjacent to the matrix and the external surface of the skin is facing away from the matrix. In a preferred embodiment, the internal surface of the skin is in contact with the matrix. In this arrangement, the external surface of the skin is available for contacting with toxins or other compositions to assess their effect on the skin according to the present methods.

The matrix with the skin sample thereon is immersed in a volume of a medium sufficient to contact the matrix but not to completely cover the skin; i.e. the external surface of the skin is not submerged but is exposed above the surface of the medium. Preferably, the surface of the medium is within 0.5 to 2 mm of the upper surface of the matrix and provides aqueous contact to the skin sample through a wicking effect. For example, where the skin sample has a thickness of about 1 to 2 mm, the surface of the medium is preferably from about 0.5 to about 2 millimeters below the external surface of the skin.

The extracellular support matrix is typically soft and may indent upon placement of the skin sample thereon such that the edges of the matrix may contact the vertical edges of the skin sample.

The extracellular support matrix is pre-treated to equilibrate the matrix with the medium before the skin sample is placed thereon. Pretreatment of the matrix comprises cutting the matrix to a predetermined size and soaking the cut matrix in the medium in a sterile container for a period of time sufficient to saturate and equilibrate the matrix with the medium. A preferred soaking time is 4 hours at 37° C.

The medium contemplated by the present invention is an aqueous nutrient medium designed to promote and maintain viability of the skin sample. A preferred medium is Eagles Minimum Essential Medium (MEM) supplemented with 10% (v/v) fetal bovine serum (FBS) and an antibiotic. Exemplary antibiotics are gentamicin, streptomycin, penicillin, kanomycin and the like. A preferred antibiotic is gentamicin. The final concentration of antibiotic in the medium depends upon the particular antibiotic used. Where the antibiotic is gentamicin, a preferred concentration is about 0.2 mgs per ml of medium. Other media can also be used, preferably involving the use of fetal bovine serum, or using serum-free defined media as is well known in the art.

The matrix with the skin sample thereon may be maintained in the medium for indefinite periods of time. Preferably, the medium is changed every 2 to 3 days.

After a suitable histoculturing period, a quantity of liposomes containing the selected beneficial macromolecular compound is applied to the skin histoculture. A second histocultured skin sample is treated with the compound alone as a control. The skin histocultures are then processed and prepared to asses the viability of the tissues and the skin cell undergoing the treatment, and to determine the specificity of delivery of the beneficial compound in the liposomes.

In one embodiment, viability and/or delivery is assessed by measuring the incorporation into cells of the skin sample of an indicator specific for viable cells. As used herein, the phrase "specific for viable cells" means that the indicator is taken up or incorporated into living, but not dead, cells.

The indicator specific for viable cells may be a metabolic precursor or a non-metabolite that gains access to living cells. Exemplary metabolic precursors are ribo- or deoxyribonucleic acid precursors such as purines, pyrimidines, nucleosides and nucleotides. Preferably, the metabolic precursor is operatively linked to an indicating means to facilitate detection. A preferred indicating means for a metabolic-precursor indicator is a radiolabel such as $^{35}S$, $^{32}P$, $^{125}I$, $^{3}H$ and the like. A particularly preferred radiolabeled metabolic-precursor indicator is $^{3}H$-thymidine.

A preferred non-metabolite indicator specific for viable cells is a dye that is capable of optical detection. Any dye recognized in the art as being specific for viable cells can be used in accordance with the skin toxicity assay of this invention. See, e.g., Handbook of Fluorescent Probes and Research Chemicals, ed. by R. P. Haugland, Molecular Probes, publisher, Eugene, Oreg. (1989-1991 and 1992-1993).

In a preferred embodiment, the dye is a fluorescent dye. Exemplary viable-cell-specific fluorescent dyes are BCECF-AM (B-1150), Calcein-AM (C-1430), CFDA (carboxyfluorescein diacetate; C-195) Acridine orange (A-1301), Calcein blue (H-1426), Fura-2AM (F-1201), Fluorescein diacetate (F-1303) or Carboxy analog (C-1431) and the like. Such dyes are well known in the art and are commercially available (Molecular Probes, Eugene Oreg.). Particularly preferred are the dyes BCECF-AM or Calcein-AM. The numerals in the parenthesis indicates the product number for the listed fluorescent dyes that are available from Molecular Probes.

In one embodiment, the incorporation or uptake of fluorescent dyes specific for viable cells depends upon metabolic activity of the viable cell. In accordance with this embodiment, non-flucrescing dyes are taken up by viable cells and converted to a fluorescing product by an intracellular enzyme such as an esterase. The presence of intracellular fluorescence indicates viability.

In another embodiment, viability is assessed by measuring the uptake or incorporation into cells of the skin sample of an indicator specific for dead cells. As used herein, the phrase "specific for dead cells" means that the indicator is taken up or incorporated only into dead, non-viable cells.

Typically, dyes specific for dead cells are compounds with a high ionic charge and low permeability such that the dyes cannot permeate intact cellular membranes. When cells die, the membrane is structurally or functionally ruptured such that dyes specific for dead cells gain access to the intracellular space where they bind to intracellular components such as nuclear membranes.

A preferred dead-cell-specific indicator is a dye capable of optical detection. A preferred dead-cell-specific dye is a fluorescent dye such as propidium iodide, ethidium bromide, ethidium homodimer [(5,5'-diazadecamethylene) bis(3,8-diamino-6-phenylphenanthridium)dichloride, dihydrochloride] and the like. most preferred is propidium iodide. Propidium iodide (PI) and other dyes specific for dead cells are well known in the art and commercially available (Molecular Probes, Eugene, Oreg.).

In still another preferred embodiment, assessing viability is accomplished by simultaneously measuring the uptake or incorporation of both an indicator specific for viable cells and an indicator specific for dead cells. Viability is assessed as the ratio of viable to dead cells. Where both the indicator specific for viable cells and the indicator specific for dead cells are fluorescent dyes, such dyes should have different emission spectra so as to facilitate discrimination between viable and dead cells. Compositions and methods for determining cell viability by the differential uptake of indicators specific for viable and dead cells and tissue culture samples are well known in the art. Haugland, Supra.

Means for detecting the uptake or incorporation of indicators specific for viable cells are dependent upon the particular indicator used and are well known to those of skill in the art. A preferred means for detecting radiolabeled metabolic-precursors is autoradiography of histological sections of the skin samples that have taken up the precursor.

A preferred means for detecting dyes is microscopic examination. Microscopic examination can involve the use of any microscope that allows one to selectively and reproducible evaluate indicator incorporation into specific cells of the skin sample at varying locations within the three-dimensional, native-state skin histoculture.

Typically, the microscopic examination requires the capability of optical sectioning. Optical sectioning is the ability to view preselected depths within the three-dimensional structure of the skin in the absence of optical interference provided by the presence in the skin of microsomes, air bubbles, fat globules and other tissue components, which provide reflection of light and optical interference.

In addition, optical sectioning allows for viewing a variety of planes within the three-dimensional skin histoculture. By sequentially sectioning serial layers of the skin, one can produce a total picture of the skin and hair follicle or, alternatively, a picture of a region of the skin and the follicles where a particular cell type of interest is located. Thus, comparative studies of a plurality of depths or regions of the skin can be made. In this way, viability can be assessed in surface cells, at cells underneath the dermal layer, cells inside the epidermal layer, or in other specific cell types such as nerve cells, oil secreting cells, hair follicle cells.

The optical section thickness can be varied to accommodate the cell size or tissue to be observed and can range from about 0.1 to 1000 microns. Preferred sections are in the range of 0.5 to 10 microns, preferably about 2 to 6 microns.

A preferred microscope that is capable of performing optical sectioning is a confocal scanning laser microscope such as the MRC-600 CONFOCAL IMAGING SYSTEM (Bio-Rad, Richmond, Calif.), mounted on a Nikon Optiphot using a 10× PlanApo plan objective. Such a confocal scanning microscope has been successfully used to asses delivery (see the Examples). Other available methods for optically scanning or sectioning planes of the tissue sample are also contemplated by the present invention.

Viability is assessed at any particular location within the skin as a ratio of viable or dead cells to total cells or as a ratio of live to dead cells on the basis of the uptake of indicators specific for viable and dead cells respectively. When viability is assessed both before and after contact with a putative beneficial compound, comparing the ratio of live to dead cells as assessed before and after contact with the putative beneficial agent provides an indication of the toxicity or benefit provided by the administered compound.

The procedure for applying indicators to the skin culture varies with the particular indicator used. Typically, indicators are added to the medium about 6 hours and, preferably about 24 hours after placing the skin sample in the medium. Following addition of the indicator to the medium, the culture is maintained under culturing conditions for a period time sufficient to allow the indicator to enter and label the cells of the skin sample. Preferably, the culture is maintained in the presence of the indicator for about 5 minutes to about 2 hours and, more preferably for about 10 to 20 minutes.

The concentration of indicator added to the medium varies with the particular indicator used. Where the fluorescent dyes PI and BCECF-AM are used, the dye concentration is from about 1 to about 100 micromolar, preferably from about 2 to about 50 micromolar, and more preferably about 5 micromolar each.

Exemplary in vitro skin histoculture methods are described in the Examples.

The in vitro histoculture assay can be utilized in a variety of ways. The assay can be utilized to evaluate and optimize liposome formulations for enhanced efficacy of delivery of the beneficial compound, or to study other aspects of the liposomes usefulness in the targeting formulation. Furthermore, the assay can be used as a screening system to identify additional beneficial compounds for treating conditions afflicting hair follicles as described further herein.

In addition, the in vitro histoculture assay methods can be utilized to determine the effective dosages of beneficial compounds for use in the present methods.

2. Preparation of Liposomes Encapsulating Beneficial Compounds, and Liposome Compositions A beneficial liposome composition of the invention is typically provided in one or more of a variety of compositional forms suitable for the contemplated use. Although proteins, nucleic acids or other compounds for use in a liposome generally retain biological activity in a variety of buffers and solutions, it is preferred to be formulated in a phospholipid composition. Particularly preferred are phospholipid compositions which afford maximum stability and biological activity of the beneficial compound in the composition. Such phospholipid compositions are preferably formulated to form liposome compositions, as are generally well known in the art. Typically, the composition contains an amount of biologically active beneficial compound suitable for its contemplated use.

The preparation of liposomes, and their use in drug therapy has been previously described. See, for example, U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference. Exemplary methods for the entrapment of nucleic acids into liposomes are described by Hoffman et al., *FEBS Ltrs* 93:365-68, 1978 and in U.S. Pat. No. 5,223,263, hereby incorporated by reference herein.

Preferred and exemplary methods for preparing beneficial compound-encapsulated liposomes for use in the present methods are described in the Examples. In particular, the encapsulation of melanin, protein or nucleic acid, each for delivery to hair follicles as a beneficial compound, are described herein.

The liposome compositions of the present invention typically comprise about 0.1 mg to about 3 mg of protein, or about 0.1 ug to about 0.5 mg nucleic acid, per mg of phospholipid mixture.

The ratio of active compound to phospholipid mixture may determine the sensitivity of the resulting reagent. Thus, use of a ratio of about 1 to 2 mg protein per mg phospholipid mixture may be suitable for a protein reagent having a International Sensitivity Index ("ISI") of about 1.0. Use of a ratio of about 0.25 to about 0.5 mg protein per mg phospholipid mixture may be suitable to prepare a composition having an ISI of about 1.6 to about 2.0.

Preferred are compositions that additionally comprise from about 0.5 to about 1.5% (w/v) glycine. Where it is desired to be able to lyophilize the liposome composition to allow storage and later reconstitution, the reagent preferably includes a cryopreservative, preferably a carbohydrate preservative, most preferably trehalose.

The lipid bilayer of the liposomes comprises phospholipids, preferably, phosphoglycerides. Exemplary liposome compositions include phosphatidylcholine (PC) liposomes, particularly egg PC (EPC) and dipalmitoyl PC (DPPC). Additional candidate liposome compositions are prepared according to the teachings of U.S. Pat. No. 4,394,488, the teachings of which are incorporated by reference, particularly the descriptions of liposomes comprising phosphotidylethanolamine (PE), phosphotidylserine (PS), sphingolipids, phosphotidylglycerol (PG), phosphatidic acid (PA), cholesterol, spingomyelin cardiolipin, various cationicphospholipids glycolipids, gangliosides, cerebrosides and the like, used either singularly or in combination.

"Phospholipid" refers to an organic molecule derived from either glycerol (most commonly) or sphingosine. Phospholipids derived from glycerol (or phosphoglycerides) comprise a glycerol backbone, two fatty acid chains esterified to the first and second carbons of the glycerol and phosphoric acid esterified to the third carbon. Optionally, an alcohol moiety is esterified to the phosphoric acid.

Suitable phospholipids for use in the liposome compositions of the present invention include those which contain fatty acids having twelve to twenty carbon atoms; said fatty acids may be either saturated or unsaturated. The phospholipids may come from any natural source and the phospholipids, as such, may be comprised of molecules with differing fatty acids. Phospholipid mixtures comprising phospholipids from different sources may be used. For example, PC, PG and PE may be obtained from egg yolk; PS may be obtained from animal brain or spinal chord. These phospholipids may come from synthetic sources as well.

Phospholipid (PL) mixtures having a varied ratio of individual PLs may be used. However, although the phospholipids may be used in varied ratios, mixtures of phospholipids having preselected amounts of individual phospholipids result in liposome compositions having advantageous activity and stability of activity. Thus although a wide range of ratios of individual phospholipids may be used, for advantageous activity and stability of the resulting liposome composition, certain phospholipid compositions are preferred.

The phospholipids are conveniently combined in the appropriate ratios to provide the PL mixture for use in preparing the liposome composition of the present invention.

Liposomes are preferably prepared using one or more phospolipids including (N-(1-(2,3-dioleolyoxy)propyl)-N,N,N-trimethyl ammonium chloride) (DOTMA), dioleoylphosphatidylethanolamine (DOPE), diolecylphosphatidylcholine (DOPC), phosphatidylethanolamine (PE), egg PC (EPC), phosphatidylcholine (PC), dipalmitoyl PC (DPPC), cholesterol and the like phospholipids. Phospholipids can be obtained from a variety of sources, including Avanti (Birmingham, Ala.), GIBCO BRL (Gaithersburg, Md.) and Aldrich (Milwaukee, Wis.), or can be prepared from available materials, as is well known.

Preferred liposomes comprise PC, EPC, or DPPC homogeneously. Further preferred liposome compositions comprise a combination of a PC-type phospholipid (such as PC, EPC, DOPC, DPPC and the like) combined with a PE-type phospholipid (PE, DOPE and the like) in a molar ratio of from about 2:5 to about 5:2, more preferably about 5:2 PC:PE. A preferred liposome composition comprises PC:PE:Chol in a molar ratio of 5:2:3.

A preferred liposome for use in the present invention additionally includes cationic phospholipids. One preferred cationic phospholipid is a monocationic phospholipid having two identical alkyl side chains.

Preferred cationic phospholipids are also generally available from a variety of sources, including the above recited sources. Particularly preferred cationic phospholipids include cationic phospholipids such as D282, D378, D383, D3886, D3897 and D3899, obtainable from Molecular Probes (Eugene, Oreg.), the structure and synthesis of which is well known and described in Handbook of Fluorescent Probes and Research Chemicals, ed. by R. P. Haugland, Molecular Probes, publisher, Eugene, Oreg. (1989-1991, and 1992-1993). The structures of cationic phospholipids D282, D378, D383, D3886, D3897 and D3899 are shown in FIG. 8.

D282 is also known as 1,1'-dioctadecyl-3,3,3',3'-tetramethylindocarbocyanine perchlorate; D378 is also known as 3,3'-diheptyloxacarbocyanine iodide; D383 is also known as 1,1'-didodecyl-3,3,3',3-tetramethylindocarbocyanine perchlorate; D3886 is also known as 1,1'-dioleyl-3,3,3',3'-tetramethylindocarbocyanine methanesulfonate; D3897 is also known as N-4-(4-dilinoleylaminostyryl)-N-methylpyridinium iodide; and D3899 is also known as 1,1-dilinoleyl-3, 3,3',3'-tetramethylindocarbocyanine perchlorate.

In one embodiment, the liposome composition of this invention contains one or more of the above cationic phospholipids. Preferably, a liposome composition of this invention comprises a formulation of phospholipids comprising a mixture of (a) one or more of the phospholipids PC, EPC, DOPC, DPPC, PE, DOPE, cholesterol and the like phospholipids, and (b) one or more of the cationic phospholipids D282, D378, D383, D3886, D3897, D3899 and the like. A particularly preferred liposome composition comprises a mixture of phospholipid (a) and cationic phospholipid (b) in a ratio of about 0.5 to 2.0 moles of phospholipid (a) to about 0.5 to 1.5 moles of phospholipid (b), and more preferably about 1.0-1.2 moles of phospholipid (a) to 0.8 moles of cationic phospholipid (b). A preferred phospholipid composition in this embodiment comprises a mixture of DOPC or DOPE with one or more of the above cationic phospholipids in a ratio of about 0.8 moles to about 1.0-1.2 moles.

In another embodiment, the invention comprises a liposome composition comprising one or more phospholipids selected from the group consisting of PC, EPC, DOPC, DPPC, PE, DOPE and cholesterol, combined with one or more phospholipids to form pH-sensitive liposomes. pH-sensitive liposomes are generally well known and their preparation has been described by Straubinger et al., *FEBS Letts.* 179:148-154, 1985. A preferred pH sensitive liposome comprises oleic acid (OA) and PE at a molar ratio of 3:7. OA is available from a variety of commercial sources, including Sigma (St. Louis, Mo.). Several pH-sensitive liposome systems have been described. There are two main categories: intrinsically pH-sensitive liposomes and those which utilize an external non-lipid trigger. Intrinsically pH-sensitive liposomes are constructed by combining phosphatidylethnolamine (PE) with one of a number of acidic amphiphiles. Externally triggered pH-sensitive liposomes combine an otherwise stable liposome with an external soluble component such as a titratable polymer or a titratable synthetic peptide which undergoes a conformational change upon acidification. To increase the efficacy of intracellular delivery, liposomes can be made pH-sensitive and able to fuse with cellular membrane at decreased pH values (pH drop from 7.4 to 6.5) or in the presence of polyethylene glycol. Some pH-sensitive liposomes are composed of DOPE: Cholesterol hemisuccinate at molar ratios 2:1.

The preferential targeting of a liposome composition of this invention to the hair follicle can be optimized by the choice of phospholipids in the liposome composition, and may depend additionally on the included beneficial compound. Optimization can be readily conducted by use of the in vitro histoculture assay method described herein by preparation and testing of a panel of preselected liposome formulations according to the phospholipid parameters described herein.

Particularly preferred parameters for targeting beneficial compounds to hair follicles include the combined use of liposomes that have both cationic lipids and are pH-sensitive.

Where the liposome composition will be lyophilized prior to storage for later use, it is preferred to include a carbohydrate or carbohydrates as cryopreservative(s) to protect the integrity of liposomes in the resulting liposome composition during lyophilization and subsequent rehydration.

Cryopreservation relates to preserving the integrity of delicate substances when liquids containing them are frozen and dehydrated. The use of a carbohydrate as a cryopreservative of liposome integrity upon freezing and subsequent lyophilization has been reported (Racker E., *Membrane Biol.* 10:221-235, 1972; Sreter F. et al., *Biochim. Biophys. Acta.* 203:254-257, 1970; Crowe et al., *Biochem. J.* 242:1-10, 1987; Crowe et al., *Biochim. Biophys. Acta.* 987:367-384, 1988.

Suitable carbohydrate cryopreservatives include trehalose, maltose, lactose, glucose and mannitol. According to a preferred aspect of the present invention, trehalose is included in aqueous buffer solution used in the preparation of a liposome composition of the present invention (prior to lyophilization), preferably at a concentration in the range of about 50 mM to about 250 mM.

The phospholipids, which may be obtained from the manufacturer in an organic solvent, are mixed together in the appropriate ratios to yield the specified composition. An antioxidant can also be added to reduce alkyl chain peroxidation of the fatty acid portions of the phospholipids, and the organic solvent, if present, is removed by evaporation. One suitable antioxidant is butyrated hydroxy toluene. Preferably about 0.1% (by weight) of antioxidant is used.

The dried (evaporated) phospholipid mixture is then redissolved with an aqueous detergent solution. Suitable detergents include those which have a relatively high critical micelle concentration (CMC) (Womack et al., *Biochim. Biophys. Acta* 733:210, 1983). Such detergents include detergents having a CMC of greater than approximately 2 mM. Preferred are those detergents having a CMC of between approximately 2 to 25 mM. Such preferred detergents include 3-[(3-cholamidopropyl)dimethylammonio]-1-propanesulfonate (CHAPS) and alkylglucopyranosides such as octyl beta-D-glucopyranoside, octyl beta-D-thioglucopyranoside and the like. Optionally, the detergent solution may include other components. These components may include buffer salts such as HEPES, Tris, phosphate, and the like; various other salts such as NaCl, KCl, and the like; a carbohydrate cryopreservative such as trehalose, maltose, glucose, and the like; and glycine.

According to a preferred embodiment of the present invention, the detergent solution comprises 20 mM Tris, pH 7.5, 150 mM NaCl, (TBS) containing 100 mM CHAPS, 150 mM trehalose and 0.8% glycine. According to this preferred embodiment, the phospholipids are redissolved in this solution to give a final concentration of about 20 mg/ml.

Purified proteins for use in a liposome, together with carrier protein, are combined with the redissolved phospholipids and the volume of the resulting mixture is adjusted with a buffer as described above, preferably containing cryopreservative (most preferably trehalose) and glycine but no detergent. Protein is admixed with carrier protein, such as bovine gamma globulin, and sufficient buffer is added to adjust the final concentrations of active protein to 10 mg/ml, bovine gamma globulin to 1 mg/ml, phospholipid to 4 mg/ml and detergent to 20 mM. Suitable buffers include TBS containing 150 mM trehalose and 0.8% glycine.

The resulting clear, colorless solution requires no vortexing or sonicating to ensure co-solubilization.

The detergent in the phospholipid admixture can be removed by a number of methods resulting in a stable liposome composition having a protein or nucleic acid associated with and inserted through the lipid bilayer. Suitable methods of removal of detergent include dialysis, tangential flow diafiltration, cross flow hollow fiber filtration, treatment with hydrophobic chromatography resin, and simple dilution.

One preferred method of detergent removal from the phospholipid admixture utilizes dialysis for at least 30 hours at room temperature in dialysis membrane tubing against a buffer such as TBS containing 150 mM trehalose, 0.8% glycine and 0.05% $NaN_3$ to remove the detergent. Another preferred method of detergent removal utilizes resin treatment. Suitable resins include hydrophobic chromatographic resins such as Amberlite XAD-2 (Rohm and Haas Co. in Philadelphia, Pa.) or Bio-Beads SM-2 (BioRad in Richmond, Calif.). The resins may be used to remove the detergent, either by direct contact with the phospholipid solution admixture or separated from it by a dialysis membrane. The rate of removal of detergent from the phospholipid admixture is proportional to the weight ratio of the detergent in solution and the chromatographic resin beads.

The liposome solution resulting from the detergent removal step is then made to 5 mM $CaCl_2$. According to one preferred aspect, the liposome composition which contains the fully active compound is diluted to a concentration of 50 mM Tris, pH 7.5, 75 mM trehalose, 0.8% glycine and 10 to 15 mM $CaCl_2$ before use. Alternatively, the diluted reagent may be lyophilized for long term preservation of its biological performance characteristics and then later reconstituted by suspension in water before use.

Another preferred method of detergent removal avoids the use of either dialysis or resin treatment and yet provides for preparation of active reagent. According to this method, detergent solubilized phospholipid compositions containing protein or nucleic acids are diluted into a buffer without detergent to produce mixed micelles containing the beneficial compound which remain capable of being fully activated by $CaCl_2$. According to this aspect of the invention, phospholipids are dissolved to 20 mg/ml in a buffer containing detergent, preferably an alkyl glucopyranoside. A suitable buffer-detergent solution comprises 20 mM HEPES (pH 6) containing 50 mM octyl beta-D-thioglucopyranoside (OTG) and 150 mM NaCl. Carrier protein, active protein or nucleic acid, and $CaCl_2$ are then added and the mixture diluted further with buffer without detergent, such as 20 mM HEPES (pH 6) containing 150 mM NaCl, to yield final concentrations of active protein or nucleic acid at about 10 mg/ml, carrier protein (bovine gamma globulin) at 1 mg/ml, $CaCl_2$ at 5 mM, phospholipids at 4 mg/ml, and OTG at 10 mM. The reagent may be lyophilized for storage as described above, or diluted as described above before use.

According to another aspect of the present invention, this reagent may be prepared by following methods for the preparation of vesicles and detergent-phospholipid mixed micelles from phospholipids by methods based on mechanical means, by removal of organic solvents, by detergent removal, and by size transformation as has been described by Lichtenberg, D. and Barenholz, Y., Methods of Biochemical Analysis, 33: 337-462 (1988), and the disclosures of which are incorporated herein by reference.

Incorporation of a beneficial compound is conducted by incorporation of the compound in the liposome either during liposome formation, or after formation by combining the liposome with the compound. Methods of introducing the compound into the liposome can vary, and are not intended to be limiting. Preferred methods are described in the Examples.

Where nucleic acid is entrapped into a phospholipid composition, a wide variety of ratios of nucleic acid to phospholipid may be utilized as discussed earlier. However, it is preferred to use about 100 micrograms (ug) of nucleic acid (in the form of double-stranded DNA such as plasmid DNA) with about 0.1 to 10.0 milligram (mg) phospholipid. Where cationic phospholipids are to be utilized in a phospholipid composition, it is particularly preferred to use about 100 ug nucleic acid to from 0.2 to 1.2 micromoles (umole) of phospholipid, particularly 100 ug nucleic acid to 0.8 umole.

Preferred liposome compositions of this invention comprise a liposome containing an effective amount of a beneficial compound of this invention. Preferred beneficial compounds depend upon the use of the liposome composition as described further herein, and can include melanin, hair dyes, tyrosinase, nucleic acids, including sense and antisense nucleic acid molecules, hair color-restoring agents, hair growth-promoting agents, and agents which confer chemoresistance to the targeted hair follicle.

3. Hair Follicle-Targeted Drug Therapy

Results of studies herein on liposome-mediated delivery show that the beneficial macromolecular compound is concentrated at the hair follicles and has been transported across the cell membrane and through the cytoplasm and in some cases to the nucleus. The liposome-incorporated material (beneficial compound) is preferentially delivered to the hair follicle, because the levels of the beneficial compound in the adjacent skin tissue is substantially lower than in the hair follicles. Due to the unusual selectivity of delivery to the hair follicle when using the disclosed liposome formulations, and based on the degree of selectivity based on the compound to be delivered and the liposome formulation utilized, this selectivity is referred herein to as "directed delivery", "preferential delivery", "selective delivery" and in some cases as "exclusive delivery", depending upon the relative amount of material delivered to the hair follicle tissue as compared to the adjacent skin tissue. In addition, the selectivity can be expressed in terms of the selectivity of pharmaceutical effect upon the hair follicle tissue as compared to the adjacent skin tissue.

With the tissue sample treated with the macromolecular compound where the compound had not been incorporated in liposomes, very little reaches the follicle cell or follicle cell nuclei. Thus, the liposome-based system specifically, selectively, and efficiently targets the hair follicles with compounds that otherwise do not concentrate at the hair follicles.

In one embodiment, the invention describes methods for selective and beneficial targeting of therapeutic compounds and compositions to the hair follicle of a mammal.

Based on the present disclosure, it is determined that compounds and compositions, particularly polymers, dyes, proteins, nucleic acids and macromolecules, are specifically delivered to hair follicle tissue, so long as the compounds or compositions are encapsulated in liposomes.

The invention contemplates the delivery of a wide variety of beneficial or otherwise therapeutic compounds to the hair follicle, with the selectivity of delivery to the hair follicle over adjacent skin tissue cells being of particular importance, and the primary result according to the present methods. Thus, the therapeutic compounds can be nucleic acids, hormones, proteins, small molecules, enzymes, steroids, vitamins and other biochemical co-factors deemed to provide a therapeutic effect upon the hair follicle cell's growth, condition, color and the like.

Thus, a beneficial compound for use in the methods and compositions of this invention can be any of a variety of molecules including molecules that would not otherwise be able to reach hair follicles, such as macromolecules and polymers that are too large to penetrate stratum corneum or lipid barriers such as cell membranes, and lipophobic molecules that are not able to penetrate lipid barriers due to their chemical properties. Additional beneficial compounds for use in the present invention include lipophilic compounds that do exhibit a capacity to interact with and penetrate lipid barriers, but which can penetrate other tissue barriers such as dermis where the compound can exhibit potentially undesirable effects upon cells external to the hair follicle. Thus, a beneficial compound can be a macromolecule, a polymer, a lipophobic molecule, a lipophilic molecule having undesirable effects on cells external to the hair follicles, and the like compounds.

Particularly preferred are agents (beneficial compounds) which improve the growth of the hair shaft, agents which stimulate the production of hair coloring pigments in the hair follicle, agents which replace pigment in the follicle cell or hair shaft or which color (dye) the hair shaft (i.e., restore hair color), agents which stimulate hair growth, and agents which prevent hair loss (alopecia).

Agents useful for restoring or pigmenting hair color include melanin or hair dyes, which directly color hair as a pigment, the protein tyrosinase, which is an enzyme which catalyzes the production of melanin pigment precursors and thereby increases pigment production in hair follicle cells, and nucleic acids which encode and express tyrosinase and other proteins which stimulate hair growth or prevent hair loss. By "tyrosinase" is meant the protein tyrosinase or any derivatives, variants, analogs, or fragments thereof which are useful in the present invention. Such useful derivatives, variants, analogs, or fragments are defined by their ability to catalyze the production of melanin pigment precursors. The term "fragment" includes any form of tyrosinase that does not include the complete amino acid sequence of tyrosinase. The term "derivative" as used herein refers to a peptide or compound produced or modified from another peptide or compound of a similar structure. This could be produced in one or more steps. The term "modified" or "modification" as used herein refers to a change in the composition or structure of the compound or molecule. However, the activity of the derivative, modified compound, or molecule is retained, enhanced, or increased relative to the activity of the parent compound or molecule. This would include the change of one amino acid in the sequence of the peptide or the introduction of one or more non-naturally occurring amino acids or other compounds. This includes a change in a chemical body, a change in a hydrogen placement, or any type of chemical variation. In addition, "analog" as used herein refers to a compound that resembles another structure. An analog is not necessarily an isomer. The above are only examples and are not limiting.

As is well known, melanin is a polymer of tyrosine that occurs in a variety of forms and polymer lengths. Thus, the use of the term "melanin" is intended to mean melanin in any of its forms which can be utilized in the present invention. Also contemplated for use in this invention are derivatized melanin, extracted melanin, modified melanin, and the like variants of melanin which have the desirable property of providing hair pigment. Such variants include derivatives of melanin including compounds or polymers produced from tyrosine or modified from another compound, amino acid, or polymer of similar structure. The term "modified" or "modification" as used herein refers to a change in the composition or structure of the compound or molecule. However, the activity of the derivative, modified compound, or molecule is retained, enhanced, or increased relative to the activity of the parent compound or molecule. This includes a change in a chemical body, a change in a hydrogen placement, or any type of chemical variation.

Hair dyes are also extremely well known, and can take a wide variety of forms that need not limit the present invention. In particular, it is noted that hair dyes are typically aromatic compounds which are incidentally mutagenic or otherwise exhibit undesirable effects of various tissues of the body such as cells external to a hair shaft or hair follicle, such as in the dermis or in the circulation. Therefore it is to be emphasized that the present invention provides the advantage by virtue of selective delivery to the hair follicle of reducing the extent of contact of administered hair dye with dermis and other tissues external to the hair follicle.

Agents useful in conditions of hair loss (alopecia) are those which stimulate hair growth, those which inhibit the hair loss, and those which inhibit the conditions that cause hair loss, such as chemotherapeutic agents.

Hair growth stimulators are generally well known, and include minoxidil, substance-P, cyclosporin, cyclosporin A, finesteride, and the like known hair growth stimulators.

Alopecia may be caused by numerous genetic and environmental factors, including but not limited to, stress, autoimmunity, and androgens. Agents useful in conditions of stress induced alopecia would be those that inhibit the delivery, to the cells in the hair follicle, of factors that cause the stress induced alopecia or those that protect the follicle cells from such factors. Compounds that would be useful in preventing hair loss caused by autoimmunity (alopecia areata) would be those that inhibit the response of cells in the hair follicle to antibodies or other agents of the immune response (Sundberg et al., *J. Invest. Dermatol.* 104:32S-33S, 1995; Szafer et al., *J. Invest. Dermatol.* 104:22S-24S, 1995). For example, such compounds would include, but are not limited to, steroids which are known by those of ordinary skill in the art to suppress the immune response. Another example of a compound useful in the invention would be a compound that blocks the receptors on cells in the hair follicle which are targeted by the immune system in alopecia. Cell cycle inhibitors could also prevent alopecia caused by such agents or stress by keeping the hair follicle cells in the more protected $G_1$-phase of the cell cycle.

An example of alopecia caused by androgens (androgenic alopecia) is typical male pattern baldness. The invention includes within its scope the prevention of androgenic alopecia by delivery of compounds that prevent androgenic alopecia to the hair follicle. Such compounds include, but are not limited to, compounds that block the androgen receptors on cells in the hair follicle such as steroids, steroid analogs, androgen receptor antagonists, proteins, small molecules, or nucleic acid molecules.

In preferred embodiments, the delivered compounds are antisense nucleic acid molecules which hybridize to an androgen receptor gene, thereby inhibiting androgen receptor expression. In other preferred embodiments, androgenic alopecia is prevented by the selective delivery of antiandrogens. By "antiandrogen" is meant a factor or molecule which interferes with the ability of an androgen, such as testosterone, to activate an androgen receptor. Such antiandrogens include, but are not limited to, 5-α-reductase inhibitors such as finesteride. 5-α-reductase inhibitors interfere with the ability of testosterone to activate androgen receptors by converting testosterone to dihydrotestosterone. The direct and selective delivery of antiandrogens and androgen receptor blockers to the hair follicle of the present invention advantageously avoids the side effects that may be caused by the presence of such antiandrogens and androgen receptor blockers in the bloodstream and in non-hair follicle cells.

A preferred embodiment involves the prevention of hair loss (alopecia) during chemotherapy where a patient experiences chemotherapy-induced hair loss due to the effect of the chemotherapeutic agent on the hair follicle and surrounding tissue. Thus the invention contemplates the use of inhibitors of the deleterious effects of a chemotherapeutic agent. By virtue of the selective application of the inhibitor to the hair follicle by the liposome-mediated delivery methods of the present invention, inhibition of a chemotherapeutic agent is localized to the hair follicle and therefore does not interfere with the intended systemic activity of the administered chemotherapeutic agent. In this embodiment, a preferred inhibitor of chemotherapy-induced alopecia is a gene product of the multiple drug resistance (MDR) gene, preferably the p-glycoprotein expressed by the human MDR-1 gene. Administration of a nucleic acid comprising an expression vector capable of expressing human p-glycoprotein via liposomes to the hair follicle provides intracellular human p-glycoprotein, and reduces the toxic effects of the chemotherapy upon the hair follicle, thereby reducing alopecia induced by the chemotherapy.

Another embodiment of the invention is an in vitro model of chemotherapy induced alopecia. The in vitro model may be used to screen for compounds which may prevent chemotherapy induced alopecia. Such an in vitro system may also be used to screen for chemotherapeutics which do not cause alopecia.

Thus, one aspect of the invention includes a method for inhibiting alopecia in a mammal comprising applying a therapeutically effective amount of a liposome composition to a skin area on a mammal having a plurality of hair follicles, said liposome composition comprising a liposome containing a therapeutically effective amount of a compound capable of inhibiting alopecia when delivered to said hair follicles and said liposome is capable of selectively delivering said compound to said hair follicles.

In one aspect, the alopecia is androgenic. In another aspect, the alopecia is alopecia areata. In a preferred aspect, the compound is a steroid or a steroid analog.

In another aspect, the alopecia is induced by stress. Therapeutic compounds useful for inhibiting stress-induced alopecia include, for example, cell cycle inhibitors as described herein.

In one aspect, the alopecia-inhibiting compound delivered to the hair follicles is a protein. In another aspect the alopecia-inhibiting compound delivered to the hair follicles is a nucleic acid capable of expressing in cells of said hair follicles a protein that inhibits alopecia.

Another embodiment contemplates the use of the human transformation growth factor-alpha (TGF-α) gene to reverse the "wavy" hair phenotype. See for example, Mann et al., *Cell* 73:249-261, 1993, and Luetteke et al., *Cell* 73:263-278 1993. Therefore the invention contemplates the use of a cDNA expression vector that expresses the TGF-α gene as a beneficial compound to reduce the incidence of wavy hair where the deficiency of TGF-α gene is the cause of the wavy hair phenotype.

The invention additionally contemplates the administration of any gene beneficial to hair follicles. A gene is beneficial to hair follicles where it confers, upon selective delivery to the hair follicles by the present methods, a beneficial effect upon the hair follicle. Exemplary beneficial genes include genes normally and preferentially expressed in hair follicle, and therefore important for normal gene function. Beneficial genes can be identified by any of a variety of molecular biological methods. For example, a cDNA library of expressed genes can be prepared from hair follicle tissue supporting healthy hair, and can be enriched by subtractive hybridization against a cDNA library derived from a non-hair-producing or vellus-hair-producing follicle tissue, thereby producing a library of cDNA molecules whose expression is specific to hair follicles. Individual cDNA molecules from the hair specific cDNA library can be further screened for therapeutic effectiveness using the skin histoculture assay described herein.

Particularly preferred is a gene capable of stimulating hair growth, referred to as a hair growth stimulating gene. A hair growth stimulating gene is any nucleic acid which stimulates hair growth upon administration of the gene to hair follicles of skin according to the present liposome-mediated delivery methods. A hair growth stimulating gene can be prepared from the hair specific cDNA library described above. The hair growth stimulating gene can be selected from the hair specific cDNA library by a variety of methods. The gene can be identified by subtractive hybridization using a cDNA library prepared from skin tissue which has vigorous hair shaft production against a cDNA library prepared from skin tissue which is deficient in vigorous hair shaft production, such as patches of skin where hair is absent or thinning. Such areas of skin have hair follicles but the follicle cells are experiencing changes in gene expression which affect the condition of the hair, particularly the rate of hair shaft growth. The resulting cDNA library following subtractive hybridization against the hair growth deficient cDNA library is further screened in the in vitro skin histoculture assay for cDNA molecules capable of stimulating hair growth to identify hair growth stimulating genes. Methods for isolating cDNA libraries and for conducting subtractive hybridization a well known in the art, and are not to be considered as limiting to the present invention.

Agents that may be useful for regulation of hair growth, either delivered directly or in the form of a nucleic acid which encodes an agent and is capable of expressing the agent in hair follicle cells include, for example, parathyroid hormone-related protein and Bcl-2 (Wysolmerski et al., *Proc. Nat'l Acad. Sci. USA* 91:1133-37, 1994; Holick et al., *Proc. Nat'l Acad. Sci USA* 91:8014-16, 1994; Hayman, et al., *J. Pathol.* 158: 293-96, 1989; and Veis et al., *Cell* 75:229-40, 1993). Other such agents are known to those of ordinary skill in the art. Examples included by way of example only are reviewed in Messenger, *J. Investigative Dermatol.* 101:4S-9S, 1993. An antisense nucleic acid molecule against a gene that encodes a protein that inhibits hair growth, such as fibroblast growth factor-5 (FGF-5) is another example of a potential selective liposome-mediated hair follicle therapy (Hebert et al., *Cell* 78:1017-25, 1994), hereby incorporated by reference herein. Thus, in an aspect of the present invention, a liposome composition comprising an antisense nucleic acid molecule against a hair growth-inhibiting factor is provided, as well as a method using such a liposome composition to regulate or stimulate hair growth. In preferred embodiments, the antisense nucleic acid molecule is directed against fibroblast growth factor-5.

The therapeutic agent can be delivered to the hair follicle in the form of an active formulation, such as the pigmentation protein or enzyme itself, or can be provided through gene replacement therapy, where a nucleic acid is introduced that expresses the protein to be delivered. In this mode, also referred to as gene therapy, a replacement therapy protein is provided which exerts a beneficial effect. The protein is referred to as a "replacement therapy" protein to connote that the therapy administered is to reconstitute (replace) into the tissue a protein-based function not previously present. It does not mean that a gene or protein was first deliberately removed, and then replaced.

Again, some beneficial compounds may have the ability to exhibit undesirable effects on tissues or cells external to the hair follicle, such as the dermis or other tissues accessed by the general circulation. Therefore it is noted that the selectivity provided by the present invention provides the advantage of reducing toxicity or undesirable effects of certain beneficial compounds. This is particularly important for cyclosporins useful as hair growth stimulators but which can suppress the immune system is contacted with the circulation, and for agents which confer chemoresistance in tissues where it is undesirable to provide such resistance such as in the circulation.

A therapeutic amount of a therapeutic protein in a liposome composition of this invention is an amount sufficient to produce the desired result, and can vary widely depending upon the disease condition and the potency of the therapeutic compound.

Thus, in one embodiment, the invention contemplates a method for directly and selectively delivering a beneficial compound to the hair follicles of a mammal comprising the steps of:

a) incorporating an effective amount of at least one selected beneficial compound into a liposome; and b) applying said liposomes to skin areas of the mammal having a plurality of hair follicles;

whereby said beneficial compound is preferentially transmitted to said hair follicles and enters into said hair follicles.

In a related embodiment, the invention describes a method of directly and selectively delivering a beneficial compound to hair follicles of a mammal comprising the step of applying a liposome composition of this invention topically to skin areas of a mammal having a plurality of hair follicles. The liposome composition comprises a liposome containing an effective amount of at least one selected beneficial compound wherein the liposome is capable of selectively delivering the beneficial compound to the hair follicles and whereby the beneficial compound is preferentially transmitted to the hair follicles and enters into the hair follicles.

As described, the beneficial compound can be a protein, a nucleic acid or other molecule having desirable properties upon delivery to the hair follicle cell. Where the compound is a pigment such as melanin or hair dye, or is a protein, such as tyrosinase, the objective is to restore hair color in hair as demonstrated herein. Alternatively, the compound can be aromitase or cyclosporin where the objective is to stimulate hair growth. Alternatively, the compound can be a nucleic acid encoding tyrosinase, aromitase, p-glycoprotein, TGF-α, a hair growth stimulating gene or other beneficial proteins, or can encode and express an antisense or ribozyme nucleic acid as discussed herein.

Thus, in a related embodiment, the invention contemplates a method for restoring hair color to the hair of a mammal comprising applying a therapeutically effective amount of a liposome composition to a skin area on the mammal populated with hair follicles. The liposome composition contains an effective amount of a beneficial compound capable of restoring hair color (a hair color-restoring agent). The hair color-restoring agent can be any of a variety of hair dyes, the pigment melanin, the protein tyrosinase, or a nucleic acid capable of expressing a tyrosinase cDNA as described herein.

In a related embodiment, the invention contemplates a method for inhibiting chemotherapy-induced alopecia in a mammal undergoing chemotherapy comprising applying a therapeutically effective amount of a liposome composition to a skin area on the mammal populated with hair follicles. The liposome composition contains an effective amount of a beneficial compound capable of inhibiting within the follicle cell environment the toxic effects of the chemotherapy, e.g., a protein that confers chemoresistance to hair follicle cells and hair follicles. Any compound that inhibits chemotherapy toxicity is contemplated, although the MDR-1 gene product (p-glycoprotein), or the MDR gene itself, is particularly preferred.

In a related embodiment, a method is provided for inhibiting chemotherapy-induced alopecia in a mammal, comprising applying a therapeutically effective amount of a liposome composition to a skin are on the mammal having a plurality of hair follicles, wherein the liposome composition comprises a liposome containing a cell cycle inhibitor, and the liposome is capable of selectively delivering the cell cycle inhibitor to the hair follicles. In a related aspect, the liposome contains a nucleic acid capable of expressing in the cells of the hair follicles a cell cycle inhibitor.

The introduction of chemotherapeutic agents has made a major impact on the survival of patients with leukemia, lymphoma, and testicular cancer. Among the more common malignancies of adults, carcinoma of the breast had been the most responsive to a wide variety of single agents and combination programs (Harris et al., in *Cancer: Principles & Practice of Oncology* (Devita et al., Eds.) pp. 1119-1167, 1992).

Doxorubicin is one of the most commonly used drugs for breast cancer treatment and also the most alopeciagenic among the anticancer drugs (Hussein et al., *Science*, 249: 1564-1566, 1990; Haynes et al., in *Cancer Medicine*, (Holland, Ed.) pp. 2286-2290, 1993; Harris et al., in *Cancer: Principles & Practice of Oncology* (Devita et al., Eds.) pp. 1119-1167, 1992; Weiss *Semin. Oncol.*, 19:670-86, 1992). The mode of action for its anti-cancer effect is still not certain. As a DNA intercalator, it has been shown to induce topoisomerase II mediated DNA cleavages (Tewey et al., *Science* 226:466-468, 1984). Generation of free radicals has also been proposed (Benchekroun et al., *FEBS Ltrs.* 326:302-305, 1993).

Cyclophosphamide (cytoxan), methotrexate (MTX), and 5-fluorouracil (5-FU) compose a combination (CMF) that is the most commonly used for breast cancer. Cytoxan is an alkylating agent (Harris et al., in *Cancer: Principles & Practice of Oncology* (Devita et al., Eds.) pp. 1119-1167, 1992). MTX is an antifolate; it is a competitive inhibitor of dihydrofolate reductase (DHFR), the enzyme for maintenance of intracellular reduced folate pools. Depletion of reduced folate pools results in cessation of DNA synthesis caused by lack of sufficient dTMP and purines (Fleming et al., *Semin. Oncol.* 19:707-719, 1992). 5-FU is an antimetabolite which blocks DNA precursor synthesis, and acts against DNA and RNA (Cheson et al., *Semin. Oncol.* 19:695-706, 1992).

Alopecia is a common yet distressing side effect of many cancer chemotherapeutic agents and radiation therapy (Seipp, C A in *Cancer: Principles & Practice of Oncology* (DeVita et al., Eds.) pp. 2135-2136, 1992; Cline, *Cancer Nurs.* 221-227, 1984; Merk et al., in *Hair and Hair Diseases* (Orfanos et al., Eds) pp. 601-609, 1990). As patients embark on new therapies, hair loss can induce a negative body image, altered interpersonal relationships, and often cause patients to reject potentially curative therapy (Hussein et al., *Science,* 249:1564-1566, 1990; Cline, *Cancer Nurs.,* 221-227, 1984).

The degree of hair loss is drug type dependent. Some agents are more causative than others. Doxorubicin and cyclophosphamide, commonly used for breast cancer treatment are among the worst (Haynes et al., in *Cancer Medicine* (Holland, Ed) pp. 2286-2290, 1993). Clinical trials document a consistent 85-100% hair loss in patients receiving doxorubicin (Blum et al., *Ann. Intern. Med.,* 80:249-259, 1974; O'Bryan et al., *Cancer,* 1-8, 1973). Severe alopecia occurs in 75-90% of patients treated with intravenous cyclophosphamide (Cline, *Cancer Nurs.* 221-227, 1984). A large single dose of chemotherapeutic agent may cause hair loss immediately or after 1 to 2 weeks. Smaller, multiple doses can cause hair loss in 6-8 weeks. Radiation (>500 rad) also causes hair loss (Seipp, in *Cancer: Principles & Practice of Oncology* (DeVita et al., Eds.) pp. 2135-2136, 1992; Haynes et al., in *Cancer Medicine* (Holland, Ed.) pp. 2286-2290, 1993). The severity of hair loss is dose dependent. Generally, the higher the dose, the better the therapeutic effect, and the greater the alopecia. This process is usually reversible and usually recovery is in one month after cessation of treatment (Seipp, in *Cancer: Principles & Practice of Oncology* (DeVita et al., Eds. pp. 2135-2136, 1992; Haynes et al., in *Cancer Medicine* (Holland, Ed.) pp. 2286-2290, 1993).

Several preventative methods have been proposed. Those include scalp tourniquet, scalp hypothermia, or a combination of both, the rationale of which is to reduce the blood circulation during chemotherapy (Cline, *Cancer Nurs.* 221-227, 19814; Dean et al., *N. Engl. J. Med.* 301:1427-1429, 1979; O'Brien et al., *N. Engl. J. Med.* 283:1469, 1970). None of them have been shown to have a definite protective effect, although undesirable effects, such as headaches, may arise (Hussein, *Science* 249:1564-1566, 1990; Cline, *Cancer Nurs.* 221-227, 1984).

Hair follicles have a quite complex anatomical and differentiating system. Matrix cells near the bottom of the follicle proliferate rapidly and differentiate to become parts of the growing hair shaft. They are regenerated periodically from stem cells located in a bulge surrounding the middle of the follicle. Also the system contains dermal papilla cells at the base of the bulb and mesenchymal cells outside the follicle which provide necessary factors for hair growth. Additionally, inner and outer root sheath cells connect hair follicle to the skin, and sebaceous cells provide lubrication (Colasarelis et al., *Cell* 61:1329-1337, 1990; Messenger, *J. Invest. Derm* 101:2s, 1993; Lavker et al., *J. Invest. Derm.* 101:16s., 1993).

Mammalian hair follicles undergo a life cycle. When they are producing hair they are in anagen (=growing phase of hair) and the matrix cells proliferate rapidly. Then the follicle converts through catagen phase to telogen which is a resting state. After a month or so they are reactivated to start anagen again (Colasarelis et al., *Cell* 61:1329-1337, 1990; Messenger *J. Invest. Derm* 101:2s, 1993; Lavker et al., *J. Invest. Derm.* 101:16s, 1993). It is well recognized that the hair follicle cycle is inherently programmed but can also be influenced by systemic factors that have yet to be identified (Lavker et al., *J. Invest. Derm.* 101:16s, 1993; Yuspa et al., *J. Invest. Derm.* 101: 27s, 1993).

Living cells in hair matrix multiply more rapidly than those in any other normal human tissue (Haynes, et al., in *Cancer Medicine* (Holland, Ed.) pp. 2286-2290, PA 1993). Dermal papilla cell lines have been established (Lichti et al., *J. Invest. Derm.* 101:124s, 1993). Hair matrix cells have been isolated and cultured in vitro (Reynolds et al., *J. Invest. Derm.* 101: 634-638, 1993). They are sensitive to cancer chemotherapeutic agents. Two mechanisms of alopecia caused by cancer chemotherapy have been recognized. The main one is that cytotoxic agents inhibit a specific phase of the matrix cell to cause "anagen effluvium". Scalp hair is particularly sensitive because of rapid replication in anagen of about 85% of cells, especially those on the lower matrix. A reduction in matrix volume and mitotic rate in the hair bulb after cyclophosphamide leads to a zone of diminished caliber in the hair, which then fractures easily. This process is dose dependent. At high doses there is also telogen effluvium, a cessation of cell growth caused by damage to other follicle cells. Radiation, for example, causes both (Merk in *Hair and Hair Diseases* (C E. Orfanos et al., Eds.) pp. 601-609, 1990; Tiemey et al., *Br. J. Cancer* 62:527-528, 1990).

Much less research effort has been spent on prevention of alopecia than on protection from adverse effects on bone marrow and gastrointestinal toxicity induced by antitumor agents (Hussein et al., *Science* 249:1564-1566, 1990. Schuchter et al., *Semin. Oncol.* 19:742-751, 1992; Wood, *N. Engl. J. Med.*, 312:1060, 1985). None of the current treatments for drug induced alopecia based on reducing blood circulation in the scalp have been shown to give definite protective effects in breast cancer therapy besides having undesirable effects (Hussein et al., *Science* 249:1564-1566, 1990; Seipp, in *Cancer: Principles & Practice of Oncology* (DeVita, et al., Eds.) pp. 2135-2136, 1992; Cline, *Cancer Nurs.* 221-227, 1984; Merk, in *Hair and Hair Diseases* (Orfanos et al., Eds) pp. 601-609, 1990; Jimenez, et al., *Cancer Res.* 2:5123-5125, 1992). This invention represents a novel approach to this alopecia problem. The expected advantages of this approach are as follows: no interruption of scalp blood circulation. The undesirable effects with the current treatment, such as headache (Cline, *Cancer Nurs.* 221-227, 1984) should be eliminated and the current treatments will therefore be more effective. There is a limit to the modulation of blood supply to the scalp from the outside. And a complete cutoff of blood supply could potentially cause ischemia-reperfusion toxicity. In contrast, one can use a potent antidote as desired and it can be kept on the scalp for several hours.

The present invention provides an in vitro and an in vivo model for chemotherapy-induced alopecia. An animal model for drug induced alopecia is indispensable to search for therapy. Experimental models in mice and monkeys for hair disease are available (Malkinson et al., *J. Invest. Derm.* 101: 135s-137s, 1993; Bazzano et al., *J. Invest. Derm.* 101:138s-142s, 1993; Uno et al., *J. Invest. Derm.* 101:143s, 1993). Young Fischer or Sprague-Dawley rats develop alopecia, starting from the head, in around one to two weeks after treatment with ara-C, doxorubicin, or cytoxan (Hussein et al., *Science* 249:1564-1566, 1990; Jimenez et al., *FASEB* 6:911-913, 1992; Jimenez et al., *Cancer Res.* 2:5123-5125, 1992). Alopecia induced by ara-C or doxorubicin was protected by systemic administration of ImuVert, a biological response modifier and a membrane vesicle-ribosome preparation derived from the bacterium *Serratia marcescens* by a series of lytic and centrifugal steps (Hussein et al., *Science* 249:1564-1566, 1990). Topical 1,25-dihydroxyvitamin D3 prevents alopecia induced by cytoxan or etoposide (Jimenez et al., *Cancer Res.* 2:5123-5125, 1992).

The present invention provides a method of preventing chemotherapy-induced alopecia by delivering beneficial compounds, such as cell cycle inhibitors, to the hair follicle. By temporarily stopping the growth of cells in the hair follicle causing the cells to convert from anagen to telogen, during the duration of chemotherapy, those of ordinary skill in the art will recognize that the cells in the hair follicle will not be targeted by the chemotherapeutic, and hair loss will thus be prevented. Cell cycle inhibitors known to those of ordinary skill in the art may be used to temporarily stop the growth of cells in the hair follicle during the duration of chemotherapy. Cell cycle inhibitors known to those of ordinary skill in the art include, for example, but are not limited to, p16, p15, p21, p27, and p28 (reviewed by Karp & Broder, *Nature Medicine* 1:309-320, 1995). At least one cell cycle inhibitor, p21, has been cloned and sequenced (Noda et al., *Expt'l Cell Res.* 211, 1994). Other cell cycle inhibitors are described in, for example, Paus et al., *Brit J. Dermatol.* 122:777-84, 1990; Chang et al., *Science* 267:518-22, 1995; and Bertelsen et al., *BIO/TECHNOLOGY* 13:127-131, 1995. Preferably, a nucleic acid molecule coding for a cell cycle inhibitor, in an expression vector capable of being expressed in hair follicle cells, is delivered to the hair follicle cells using the methods of the present invention.

Another aspect of the invention provides a method of screening for compounds which increase or decrease chemotherapy induced alopecia, comprising the steps of explanting skin tissue into skin histoculture as described herein, treating the skin histoculture with a liposome composition comprising the compound to be screened, having a control skin histoculture, or treating the skin histoculture with a placebo, treating the skin histoculture with an alopecia-inducing chemotherapeutic drug, measuring alopecia in the skin histoculture by physically detectable means, and comparing the skin histoculture treated with the compound to the skin histoculture treated with the placebo. The placebo may be, for example, either no treatment at all, a buffer used for the screened compound, or a compound known to not have any effect on chemotherapy-induced alopecia. The histoculture may be treated with the screened compound either before or after treatment with the chemotherapeutic drug. A preferred method of screening in vitro is set out in the examples.

In another aspect of the invention is provided a method of screening for compounds which increase or decrease chemotherapy induced alopecia in vivo. This method comprises the steps of treating mammalian skin tissue with a liposome composition comprising the compound to be screened or with a placebo, treating the skin tissue with an alopecia-inducing chemotherapeutic drug, measuring alopecia in the skin tissue by physically detectable means, and comparing the skin tissue treated with the compound to the skin tissue treated with the placebo. A preferred method of screening in vivo is set out in the Examples.

The method can be practiced on a variety of mammals, including agricultural stock such as cow, sheep, horse, goat, pig, and the like, pets such as cats, dogs or other domesticated mammals, and humans. Typically, the hair follicle is present in the skin of a mammal, and the method is practiced in vivo on a living mammal for the purpose of benefitting the condition of the hair follicle or hair shaft of the mammal.

In another embodiment, the compound delivered may be a chemotherapeutic drug. Those of ordinary skill in the art are aware that certain types of cancers, such as basal cell carcinomas, are caused by keratinocytes (Cotsarelis et al., Cell 61:1329-37, 1990). Thus, the present invention provides a means of directly and selectively delivering chemotherapeutic drugs to treat the cancerous condition by delivering the drugs directly to the keratinocytes in the hair follicle.

In another embodiment, the invention provides a method of directly and selectively delivering a compound comprising an agent that reduces skin wrinkles. Such agents may include, for example, collagen or elastic proteins. Such agents may be used to firm the skin and provide more support to the skin by strengthening the hair follicles.

In one embodiment, the selected beneficial compound is a protein which affects hair growth, alopecia, hair color or hair condition. Preferred are the proteins tyrosinase or aromitase, as well as nucleic acids coding for hair modifying proteins. In a related embodiment, the selected beneficial compound is a pigment, such a melanin.

Melanin, hair dyes and tyrosinase are preferred for their role in coloring hair. Aromitase, minoxidil and cyclosporin-A are preferred for their role in stimulating hair growth. Other therapeutic compounds suitable for use in stimulating hair growth in conditions of alopecia include cyclosporin analogs, substance P, estrogen analogs and anti-androgens. Therapeutic compounds suitable for use in preventing hair growth, such as facial or pubic hair, include alopecia inducers, catagen inducers, epidermal growth factor, and the like inhibitors of hair growth.

In another embodiment, the selected beneficial compound is a nucleic acid capable of expressing a beneficial protein which affects hair growth, alopecia, hair color or hair condition as described earlier. Preferred are the nucleic acids that express the proteins tyrosinase, aromitase, or other hair-growth stimulators, the protein products of the MDR-1 gene (i.e., p-glycoprotein) to prevent chemotherapy-induced alopecia, or enzymes which synthesize those proteins. Antisense nucleic acid molecules which target hair growth inhibitor genes such as fibroblast growth factor-5 may also be used (Hebert et al., Cell 78:1017-25, 1994).

In one preferred embodiment, the invention contemplates a method for restoring hair color in mammals, particularly man, in which the hair color is greying for any of a variety of reasons, including age. The method comprises applying a therapeutically effective amount of a liposome composition of this invention to a skin area on the mammal having a plurality of hair follicles which exhibit fading or greying hair color. The liposome composition preferably contains an effective amount of a hair color-restoring agent of this invention, such as a hair dye, melanin, tyrosinase or a nucleic acid capable of expressing human tyrosinase in the cells of the hair follicles. Preferably, the nucleic acid encodes a human tyrosinase gene including the nucleotide sequence characteristics of the tyrosinase gene sequence shown in SEQ ID NO 1.

In one embodiment, the application of the liposome composition can be repeated at defined intervals to provide prolonged effectiveness, such as prolonged hair color-restoration or prolonged chemoresistance depending on the treatment, as needed.

Insofar as a liposome composition of this invention is used therapeutically, the liposome composition is itself a therapeutic composition, and as such may also contain additional components.

Therapeutic compositions of the present invention contain a physiologically tolerable carrier together with at least one species of liposome composition of this invention as described herein, dispersed therein as an active ingredient. In a preferred embodiment, the therapeutic composition is not immunogenic when administered to a human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration upon a mammal or human without the production of undesirable physiological effects such as nausea, dizziness, gastric upset and the like.

The preparation of a pharmacological composition that contains active ingredients dispersed therein is well understood in the art. Typically such compositions are prepared as sterile compositions either as liquid solutions or suspensions, aqueous or non-aqueous, however, suspensions in liquid prior to use can also be prepared.

The active ingredient can be mixed with excipient which are pharmaceutically acceptable and compatible with the active ingredient and in amounts suitable for use in the therapeutic methods described herein. Suitable excipient are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein (e.g., protein, nucleic acid or other compounds). Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

A therapeutic composition contains a liposome composition of the present invention, typically an amount of at least 0.1 weight percent of liposome composition per weight of total therapeutic composition. A weight percent is a ratio by weight of liposome composition to total composition. Thus, for example, 0.1 weight percent is 0.1 grams of liposome composition per 100 grams of total composition.

A therapeutically effective amount of a liposome composition, or beneficial compound therein, is a predetermined amount calculated to achieve the desired effect, i.e., to effectively benefit the targeted hair follicle, depending upon the benefit to be conferred. Thus, an effective amount can be measured by improvements in one or more symptoms associated with the condition of the hair follicle or hair follicle shaft occurring in the patient.

Thus, the dosage ranges for the administration of the liposome composition of the invention are those large enough to produce the desired effect in which the condition in the hair follicle to be treated is ameliorated. The dosage should not be so large as to cause adverse side effects. Generally, the dosage will vary with the age, condition, sex and extent of the disease in the patient and can be determined by one of skill in the art.

The dosage can be adjusted by the individual physician in the event of any complication.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. Typical dosage ranges are between 50 µl to 200 µl/cm² skin surface area, preferably 100 µl/cm², of liposome composition, prepared using a ratio of liposome: therapeutic compound between 1:1 and 500:1, preferably about 4:1 to 10:1, more preferably about 8:1 to 10:1. However, suitable dosage ranges for systemic application are disclosed herein and depend on the conditions of administration. Other regimes for administration are also variable, but may be typified by an initial administration followed by repeated doses at one or more hour intervals by a subsequent administration. Regimes for administration of the liposome composition will depend on the rate of hair growth and may vary according to the individual patient. These periods may easily be adjusted by the patient's physician. Typical periods of administration range from once a day to once every two weeks. Preferably, the liposome composition will be administered from twice a week to once a week.

4. Nucleic Acid Expression Vectors for Gene Therapy

In a particularly preferred embodiment, the invention contemplates the use of recombinant DNA molecules that can function as expression vectors for expressing a beneficial protein via a liposome-mediated targeting method of this invention.

"Recombinant DNA (rDNA) molecule" refers to a DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

In living organisms, the amino acid residue sequence of a protein or polypeptide is directly related via the genetic code to the deoxyribonucleic acid (DNA) sequence of the structural gene that codes for the protein. Thus, a structural gene or DNA segment can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

The DNA segments for use in the present invention are characterized as including a DNA sequence that encodes a beneficial protein as described herein. Particularly preferred segments encode tyrosinase, aromitase, other hair-growth stimulating proteins, melanin, p-glycoprotein, TGF-α, or enzymes that synthesize those proteins. That is, the DNA segments of the present invention are characterized by the presence of a structural gene encoding one or more of the recited beneficial proteins. Preferably the gene is present as an uninterrupted linear series of codons where each codon codes for an amino acid residue found in the beneficial protein, i.e., a gene free of introns.

One preferred embodiment is a DNA segment that codes for an amino acid residue sequence that defines a tyrosinase protein corresponding in sequence to a wild type tyrosinase protein and the DNA segment is capable of expressing tyrosinase. A preferred DNA segment codes for an amino acid residue sequence consisting essentially of the tyrosinase encoding nucleic acid sequence. Human tyrosinase gene and its nucleotide sequence is well known including the cDNA sequence for expressing human tyrosinase, and has been described by Tamate et al., *J. Exp. Zool.*, 250:304-311, (1980); Shibahara et al., *J. Exp. Med.*, 156:403-414 (1989); Takeda et al., *Biochem. Biophys. Res. Comm.*, 162:984-990 (1989); Bouchard et al., *J. Exp. Med.*, 169:2029-2042 (1989); and Brichard, *J. Exp. Med.*, 178:489-495 (1993).

Insofar as there is redundancy in the genetic code, it is understood that a variety of nucleotide sequences may be utilized to express a particular amino acid residue sequence. Therefore, in one embodiment, the invention contemplates the use of a nucleotide sequence that encodes a human tyrosinase protein, preferably having the amino acid residue sequence characteristics of the amino acid residue sequence shown in SEQ ID NO 1. A particularly preferred nucleotide sequence for expressing human tyrosinase according to the present invention has the nucleotide sequence characteristics of the nucleotide sequence shown in SEQ ID NO 1.

For expression of the human tyrosinase gene, any of a variety of expression vectors may be utilized so long as the vector is compatible with expression in mammalian cells, particularly human cells. Suitable vectors are well known. A preferred vector is the pRHOHT2 vector described in the Examples, although other mammalian expression vectors are suitable.

Another preferred embodiment is a DNA segment that codes an amino acid residue sequence that defines a multiple drug resistance (MDR) gene product, preferably the MDR-1 gene product designated p-glycoprotein, corresponding in sequence to a wild type p-glycoprotein and the DNA segment is capable of expressing p-glycoprotein. A preferred DNA segment codes for an amino acid residue sequence consisting essentially of the p-glycoprotein encoding nucleic acid sequence. Human p-glycoprotein, the MDR-1 gene and the MDR-1 nucleotide sequence are well known including the cDNA sequence for expressing human p-glycoprotein, and has been described by Chen et al., *Cell* 47:381-389, 1986; Ueda et al., *J. Biol. Chem.* 262:505-508-, 1987; and Kioka et al., *Biochem. Biophys. Res. Comm.* 162:224-231, 1989.

Insofar as there is redundancy in the genetic code, it is understood that the invention contemplates the use of a nucleotide sequence that encodes a human p-glycoprotein, preferably having the amino acid residue sequence characteristics of the amino acid residue sequence shown in SEQ ID NO 2. A particularly preferred nucleotide sequence for expressing human p-glycoprotein according to the present invention has the nucleotide sequence characteristics of the nucleotide sequence shown in SEQ ID NO 2.

Another preferred embodiment is a DNA segment that codes an amino acid residue sequence that defines a transforming growth factor-alpha (TGF-α) protein corresponding in sequence to a wild type TGF-α protein and the DNA segment is capable of expressing tyrosinase. A preferred DNA segment codes for an amino acid residue sequence consisting essentially of the TGF-α encoding nucleic acid sequence. Human TGF-α gene and its nucleotide sequence is well known including the cDNA sequence for expressing human TGF-α, and has been described by Jakowlew et al., *Mol. Endocrinol.* 2:1056-1063, 1988.

Insofar as there is redundancy in the genetic code, it is understood that the invention contemplates the use of a nucleotide sequence that encodes a human TGF-α protein, preferably having the amino acid residue sequence characteristics of the amino acid residue sequence shown in SEQ ID NO 3. A particularly preferred nucleotide sequence for expressing human TGF-α according to the present invention has the nucleotide sequence characteristics of the nucleotide sequence shown in SEQ ID NO 3.

Homologous DNA and RNA sequences that encode the above beneficial proteins are also contemplated.

In another embodiment, the invention contemplates the delivery of antisense or ribozyme nucleic acids to hair follicle cells for the purpose of selectively inhibiting hair follicle gene expression, and control aspects of hair follicle cell function.

Antisense nucleic acids are generally well known in the art and function to hybridize with sense strands of messenger RNA (mRNA), thereby interfering with the normal expression of the hybridized mRNA molecule. The sequence of the antisense nucleic acid depends, as is well known, upon the nucleotide sequence of the mRNA to be hybridized. See for example, Stein et al., *Science* 261:1004-1012, 1993.

Ribozyme nucleic acids are also generally well known in the art as single-stranded (ss) RNA molecules that are capable of selectively cleaving ssRNA and ssDNA. The ribozyme is useful to selectively inhibit gene expression by cleavage of a target ssRNA or ssDNA molecule in a hair follicle cell.

Representative targets for antisense or ribozyme nucleic acids are deleterious genes in hair follicle cells, such as the genes responsible for baldness, hair loss, loss of hair color, strength or condition, and the like undesirable features of hair follicles and hair shafts. In a preferred embodiment, the invention contemplates liposome-mediated delivery of an antisense or ribozyme nucleic acid capable of inhibiting expression of the gene that produces androgen receptor, thereby inhibiting follicle cell production of the receptor, thereby reducing hair loss. Antisense nucleic acid molecules which target hair growth inhibitors such as fibroblast growth factor-5 may also be used (Hebert et al., *Cell* 78:1017-25, 1994).

The preparation and use of antisense or ribozyme nucleic acids is well known in the art, and the design of particular antisense or ribozyme nucleic acids are not themselves considered to be part of the present invention. However, insofar as the invention contemplates methods for liposome-mediated delivery of antisense or ribozyme nucleic acids to hair follicles for the purpose of improving delivery and selectivity of the effect exerted by the delivered nucleic acid, the present invention is not to be limited to any particular species thereof but rather describes general methods of their delivery as a beneficial compound.

DNA segments (i.e., synthetic oligonucleotides) used to produce a larger DNA segment that encodes a beneficial protein can easily be synthesized by chemical techniques, for example, the phosphotriester method of Matteucci et al., (*J. Am. Chem. Soc.* 103:3185-3191, 1981, or using automated synthesis methods. In addition, larger DNA segments can readily be prepared from smaller DNA segments by well known methods, such as synthesis of a group of oligonucleotides that define the DNA segment, followed by hybridization and ligation of oligonucleotides to build the complete segment.

Furthermore, DNA segments consisting essentially of structural genes encoding a beneficial protein can be obtained from recombinant DNA molecules containing a gene that defines the beneficial protein isolated from natural sources. Exemplary natural sources are described in the references cited herein where the cDNA sequences are described.

In addition, the invention contemplates the use of a recombinant DNA molecule (rDNA) containing a DNA segment of this invention. A rDNA can be produced by operatively linking a vector to a DNA segment of the present invention.

As used herein, the term "vector" refers to a DNA molecule capable of autonomous replication in a cell and to which another DNA segment can be operatively linked so as to bring about replication of the attached segment. A vector capable of directing the expression of a gene that encodes a beneficial protein is referred to herein as an "expression vector". Thus, a recombinant DNA molecule is a hybrid DNA molecule comprising at least two nucleotide sequences not normally found together in nature.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of the beneficial protein structural gene included in DNA segments to which it is operatively linked.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the beneficial protein gene in a bacterial host cell, such as *E. coli*, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmid are pUC8, pUC9, pBR322 and pBR329 available from Biorad Laboratories, (Richmond, Calif.) and pPL and pKK223 available from Pharmacia, Piscataway, N.J.

Expression vectors compatible with eucaryotic cells, preferably those compatible with mammalian cells, and particularly hair follicle cells, can also be used to form the recombinant DNA molecules for use in the present invention. Mammalian cell expression vectors are well known in the art and are available from several commercial sources. Typically, such vectors are provided containing convenient restriction sites for insertion of the desired DNA segment, and provide the signals required for gene expression in a mammalian cell. Typical of such vectors are the pREP series vectors and pEB-Vhis available from invitrogen (San Diego, Calif.), the vectors pTDT1 (ATCC #31255), pCP1 (ATCC #37351) and pJ4W (ATCC #37720) available from the American Type Culture Collection (ATCC) and the like mammalian expression vectors.

Particularly preferred are mammalian expression vectors which allow the expression of the gene in a tissue-specific manner, in this case by the action of a regulatory promotor that will limit gene expression to hair follicle cells.

Successfully transformed hair follicle cells, i.e., follicle cells that contain a rDNA molecule of the present invention, can be identified by well known techniques. For example, cells resulting from the introduction of an rDNA of the present invention can be subjected to assays for detecting the presence of specific rDNA using a nucleic acid hybridization method such as that described by Southern, *J. Mol. Biol.* 98:503, 1975, or Berent et al., *Biotech.* 3:208, 1985, or by in situ hybridization techniques well known to those of ordinary skill in the art.

In addition to directly assaying for the presence of rDNA, successful transformation can be confirmed by well known immunological methods for the presence of expressed protein. For example, follicle cells successfully transformed with an expression vector produce proteins displaying beneficial protein, which then can be assayed directly by immunological methods.

Alternatively, successful transformation of the target tissue can be confirmed by evaluation of the target tissue for indicia of function exerted by the administered beneficial compound. For example, where the compound is a nucleic acid expressing tyrosinase, as described in the Examples, the exerted function of pigmentation, or the presence of tyrosinase activity or enzymatic conversion of L-dopa to product can be detected directly in the target tissue.

B. Methods for identifying Genes That Encode Proteins Beneficial to Hair Follicles In another embodiment, the invention provides a method for identifying a gene that encodes a protein that can exhibit a beneficial effect upon a hair follicle. The method comprises the steps of (1) encapsulating a nucleic acid molecule containing the gene of interest into a liposome composition of this invention, (2) contacting the nucleic acid-containing (encapsulated) liposome with a skin sample histoculture as described herein and having at least one hair follicle, thereby delivering the nucleic acid to the follicle, and (3) observing whether the delivered nucleic acid, upon expression of any protein encoded thereon, exhibits a beneficial effect on the hair follicle. The effect observed can be changes in hair color, condition, growth rate, viability, condition of the associated hair follicle cell structures, and the like indicia of cellular response.

In one embodiment, the present method is well suited to screening gene libraries for the presence of a gene capable of expressing a protein that exhibits a beneficial effect on a hair follicle. Gene libraries can be in the form of cDNA libraries or genomic DNA libraries as is well known. The beneficial effect to be induced depends on the screening method to detect the effect, as described further herein.

The following Examples serve to illustrate particular embodiments of the invention and are not limiting of the specification and claims in any way. The examples detail the application and testing of liposome-based treatments hair follicles and hair growth problems. Parts and percentages are by weight unless otherwise indicated.

EXAMPLES

1. Liposome-Mediated Delivery of Dye to Hair Follicles

Liposome-mediated delivery of beneficial agents to hair follicles is demonstrated using a native-state skin sample histoculturing method in which hair follicle-containing skin samples are cultured allowing the growth of the hair follicle, and detailed observation of the hair follicle cells during the treatment with therapeutic liposomes.

For the histoculture of skin, pieces of shaved outbred white-haired-mouse or nude-mouse skin, approximately 2×5×2 mm, were harvested under a dissection microscope and then histocultured on collagen-gel supported sponge as described by Li et al., *Proc. Natl. Acad. Sci. USA* 88:1908-1912, 1991. Histoculture was continued for about 24 hours prior to contacting the skin histoculture with the liposome preparation.

Liposomes were prepared by sonication of about 15 mg or 25 mg, preferably 25 mg, phosphatidylcholine (PC) emulsion in phosphate buffered saline (PBS) containing about 20 mg/ml of the fluorescent dye calcein. Liposomes were also prepared by entrapping NBD-phosphatidylcholine fluorescent dye using an emulsion with about 20 mg/ml of the NBD formulation. Liposomes were separated from the non-entrapped dye by gel-filtration on a Sepharose 4B column diluted with phosphate buffered saline. The amount of entrapped dye was measured spectrofluorometrically. Two types of PC were used: egg PC (EPC) and dipalmitoyl PC (DPPC). Due to their phase transition temperatures, liposomes made of DPPC are in a gel phase at about 37° C. while liposomes prepared from EPC are in a liquid-crystalline state.

Samples of the mouse skin histocultures were incubated for about 20 minutes with each of the liposomes and with a solution of "free" calcein dye at the same concentrations used in the liposome preparation. After the tissue samples were thoroughly washed with culture medium free of liposomes to remove excess liposome composition, the specimens were analyzed with a BioRad MRC 600 laser confocal microscope with a BHS filter block, which excites the tissue at 488 nm and passes the light emitted at 520 nm. These parameters are close to the excitation and emission maxima reported for calcein, Haugland, (Ed.) *Molecular probes. Handbook of Fluorescent Probes and Research Chemicals*, Molecular Probes, Inc., Eugene, (1989-1991 and 1992-1993). There is no autofluorescence of tissue when these emission and excitation wavelengths are used. The MRC-600 Confocal Imaging System (Bio-Rad, Richmond, Calif.) was mounted on a Nikon Optiphot equipped with a 10× PlanApo Objective.

Figure 1B:
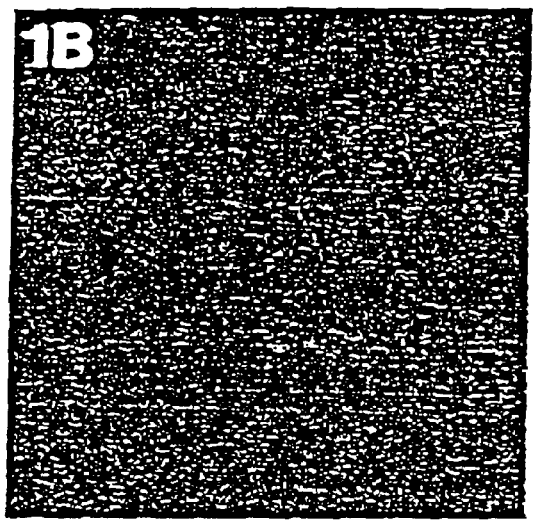
FIG. 1B is a fluorescent microscopy image (magnification 500×) of a skin histoculture treated with calcein without liposomes as described in Example 1, showing weak dye staining and no preferential delivery to skin structures.

FIG. 1A shows the skin histoculture incubated with calcein-entrapped EPC liposomes. Note the high efficiency of the delivery of the fluorescent dye preferentially into hair follicles. FIG. 1B shows the skin histoculture incubated with free calcein solution. Note the relatively low fluorescence with no preferential staining of any particular skin structure. The image in FIG. 1B was made with the same parameters of aperture and gain control as FIG. 1A.

To study the differences in liposome-mediated delivery depending upon the type of liposome used, additional liposomes were prepared as above except using DPPC in the liposome. The results obtained using either calcein or NBD-phosphatidylethanolamine as the fluorescent label showed selective labelling of the hair follicle at the surface of the follicle rather than inside the follicles when EPC was used. Thus, different liposome compositions allow even greater selectivity in delivery to a preselected region of the follicle.

The above results show a difference between substantially preferential staining of hair follicles obtained with dye entrained in DPPC or EPC liposomes compared to a lack of preferential staining of follicles over skin with free dye. Thus, liposome-entrapped dye, in contrast to free dye, becomes specifically associated with hair follicles, indicating that liposomes specifically target hair follicles. The results of this experiment have been confirmed in subsequent experiments.

Figure 9A:
FIGS. 9A and 9B contain light microscopy images of propidium iodide-stained skin histoculture treated with calcein entrapped in liposomes (9A) and free calcein (9B) as described in Example 1.
Figure 9B:

FIG. 9 demonstrates another set of experiments of liposome delivery of calcein into the follicles in histocultured skin. FIG. 9A depicts mouse skin histocultures treated with calcein-entrapped PC liposomes for 48 hours. Note the high efficiency of the delivery of the green fluorescent dye preferentially into the hair follicles and shafts. The sample has been counterstained by propidium iodide (PI) to reveal the adjacent cells of the follicles. Note that no adjacent cells or epidermal cells were stained with the green fluorescent dye. FIG. 9B demonstrates the mouse skin histocultures treated with "free" calcein dye without liposomes which is at the same concentration as were entrapped into the liposomes in FIG. 9A for 48 hours. Note the very weak staining of a few hair follicles.

FIG. 10 demonstrates liposome delivery of calcein into hair follicles in histocultured skin by topical use.

Figure 10A:
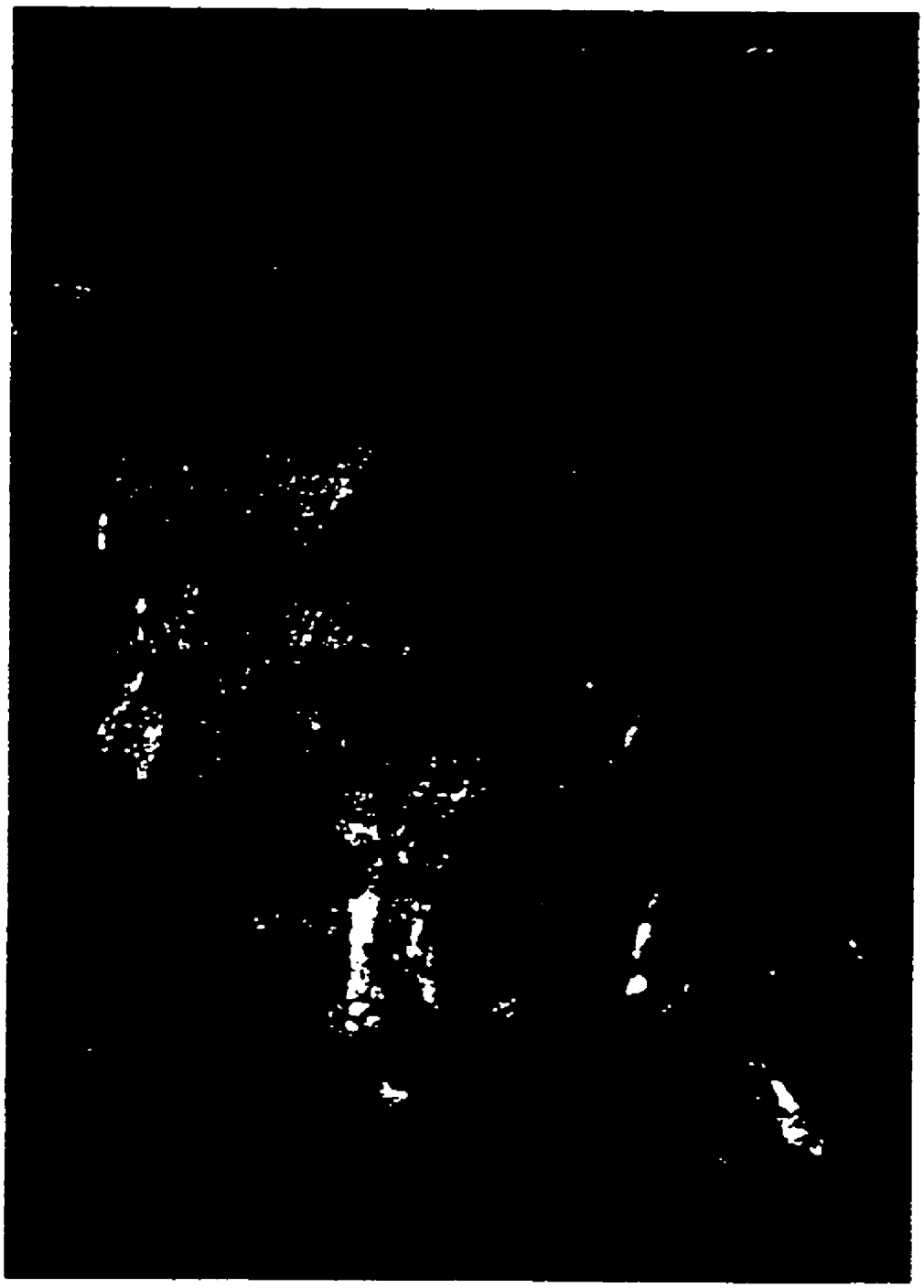
FIGS. 10A and 10B contain light microscopy images of skin histoculture treated with calcein entrapped in liposomes (10A) and free calcein (10B) as described in Example 1.
Figure 10B:

FIG. 10A shows the mouse skin histocultures topically treated with calcein entrapped in egg phosphatidylcholine liposomes for 48 hours. Note that the calcein-entrapped liposomes penetrated through the skin and delivered calcein dye into hair follicles. FIG. 10B is the control, topically treated with "free" calcein dye without liposomes which was at the same concentration as was entrapped into the liposomes in FIG. 10A for 48 hours. Noted that the "free" calcein dye rarely penetrated through the skin to stain the hair follicles, whereas the liposomally-entrapped dye was targeted very efficiently to the follicles.

2. Liposome-Mediated Delivery of Melanin to Hair Follicles

The targeted delivery of a beneficial compound to hair follicles was demonstrated using melanin as the model because melanin provides the benefit of pigmentation.

To that end, liposomes were prepared by sonication. About 20 mg of egg phosphatidycholine was rotary evaporated with a vacuum drier from a chloroform solution to form a thin film on the walls of a 5 ml round-bottomed flask for about 1 hour. The dried thin film phospholipid was suspended in about 0.5 ml phosphate buffered saline (pH 7.4) on a vortex mixer and then sonicated with a Branson probe-type sonicator fitted with a microtip at power level 3 for about 8 minutes. Then 0.5 ml of a solution of melanin (10 mg/ml) was entrapped with the above suspension by sonication for about an additional 4 minutes. Liposomes were separated from the non-entrapped melanin by gel-filtration on a Sepharose 4B column equilibrated with phosphate buffered saline.

Pieces of outbred white-haired mouse skin derived from 1-2 weeks-old animals (about 2×5×2 mm each) were harvested under a dissection microscope. The samples were then histocultured on collagen-gel supported sponges as described in Example 1. Liposome interaction with the skin was initiated after about 24 hours of histoculture. Mouse skin histocultures were incubated for about 12 hours with liposomes. As a control, a solution of "free" melanin at the same concentration as was used in the liposome preparation was also incubated for about 12 hours with pieces of the histocultured skin.

The skin histocultures were counter-stained with the dye 2',7'-bis(2-carboxyethyl)-5 which is activated to fluorescence by nonspecific esterases present only in living cells. After the tissues were thoroughly washed, the specimens were analyzed with a Nikon fluorescence microscope equipped with a fluorescein cube. Microscopically the live tissues and cells fluoresced green such that dark dense melanin deposits localized in the tissue can be clearly identified against the green background. All skin samples were then fixed with formalin and processed through dehydration, paraffinization, paraffin-embedding and hematoxylin and eoxin (H&E) staining.

Figure 2:
FIG. 2 is a hematoxylin and eosin stained paraffin-section of white-haired mouse skin treated with melanin entrapped liposomes for 12 hours, (magnification 500×) as described in Example 2, showing that the liposome-entrapped melanin primarily delivered the melanin to hair follicles as indicated by the arrows.
Figure 3:
FIG. 3 is a light microscopy image (magnification 250×) of a paraffin section of skin histoculture as in FIG. 2 stained with hematoxylin and eosin as described in Example 2, showing delivery of melanin into the hair shaft itself as indicated by the arrows.

FIG. 2 shows the liposome-mediated targeted delivery of melanin to the hair follicles in the skin histocultures stained with H&E. In the paraffin section of white-haired mouse skin treated for 12 hours with the melanin-entrapped liposomes, the majority of the melanin can be seen to be localized around the hair follicles. The melanin can be seen at the periphery of follicles and in the follicle cells themselves. FIG. 3 shows a side view of a H&E-stained hair follicle, showing that the liposome-entrapped melanin was delivered into the hair shaft itself to form the band-like melanin-distribution pattern in the terminally-differentiated keratinocytes of the typical normal pigmented hair shaft. Note that the liposome-delivered melanin seen in FIG. 3 exhibits a natural pattern in the hair shaft mimicking a natural melanized hair shaft. In the control (not shown), in which the skin histocultures had been incubated with the "free" melanin, no "free" melanin can be observed either in hair shafts or the hair follicular cells.

Thus, liposomes can specifically target an important, large, polymer to hair follicles and even enter into the hair shaft itself in a normal pattern.

Figure 11A:
FIGS. 11A-C contain images of propidium iodide histocultured skin treated with melanin entrapped in liposomes.
Figure 11B:
Figure 11C:

In order to clearly demonstrate that the liposome preferentially targeted melanin to hair follicles, additional experiments were performed in which the samples were counter-stained with propidium iodide (PI) to reveal the adjacent cells of follicles. As FIG. 11A demonstrates no adjacent cells were targeted by liposomes for melanin delivery. FIGS. 11B & 11C demonstrate the histological sections of the same samples as FIG. 11A. Note that the melanin is only observed in the hair shafts and hair follicles. No epidermal and adjacent cells of the follicles contain melanin. Therefore we conclude that the liposomes are specifically targeting melanin to the hair follicles.

Thus we have demonstrated that liposomes can specifically target an important molecule, in this case melanin, to hair follicles in histocultured mouse skin. The liposome-targeted melanin even enters the hair shaft itself in a normal pattern. Our results demonstrate the great potential for liposome-targeting of crucial substances to hair follicles to modify the hair follicle and hair itself.

Mice were then treated with the melanin-containing liposome compositions of the present invention in vivo, to produce gross coloring of the treated mouse hair.

3-4 week old white-haired mice were depilated by a mixture of bees wax and rosin gum. Topical application of liposome-melanin as described herein was started on day 6 after depilation. The liposome-melanin composition was applied on the skin of mice once per day for 4 days. The skin surface was then washed with an excess of water and wipe-dried with a gauze pad. The out-growing hair was micro-photographed. The same concentration of naked melanin solution as entrapped into liposomes was used as the control.

FIG. 12A depicts the selective delivery of melanin to the hair follicle cells, the hair shaft itself is colored, while the surrounding skin is not colored. No hair coloring is observed in the mouse treated with non-liposome entrapped (naked) melanin, as depicted in FIG. 12B.

In another experiment, 3-4 week old white-haired mice were depilated by a mixture of bees wax and rosin gum. Topical application of liposome-melanin composition was started on day 10 after depilation. The melanin used in this experiment was from Biosource, SF, CA #MM-8A-1. The liposome-melanin composition was applied on the skin of mice twice per day for 3 days. The treated skin surface was then washed with an excess of water and wipe-dried with a gauze pad. The mice were then photographed. The same concentration of naked melanin solution as entrapped into liposomes was used as the control.

FIG. 13B depicts the control mouse treated with naked melanin. The mouse's regrown hair remained white. In contrast, the regrown hair of the mouse depicted in FIG. 13A, that was treated with the liposome-melanin composition was colored, demonstrating selective delivery of melanin by the liposome-melanin compositions of the present invention.

3. Liposome-Mediated Delivery of Nucleic Acid to Hair Follicles a. Delivery of Nucleic Acids to a Cultured Cell Line The targeted delivery of nucleic acid to hair follicles was demonstrated using mouse genomic DNA cleaved to about 1 kilobase (kb) lengths as the model for nucleic acids capable of expressing protein due to the typical size of a DNA expression vector, and the size of a typical structural gene.

About 1 kb DNA was isolated from a mouse genomic DNA library and purified from low melting point agarose with the Magic DNA Purification Kit (Promega, Madison, Wis.). About 50 ng DNA was labeled with [$^{35}$S]dATP (DuPont) with the Random Primer DNA Labeling Kit (BioRad, Richmond, Calif.). The specific activity of the labeled DNA with $^{35}$S-dATP was $2.6 \times 10^{10}$ cpm/µg.

Liposomes were prepared by freezing and thawing. About 20 mg of egg phosphatidylcholine (EPC) was rotary evaporated with a vacuum drier from a chloroform solution to form a thin film on the walls of a 5 ml round-bottomed flask for about 1 hour. The dried film phospholipid was suspended in an about 0.5 ml phosphate buffered saline solution at a pH of about 7.4 in a vortex mixer and then sonicated with a Branson probe-type sonicator fitted with a microtip at power level 3 for about 8 minutes. The 0.5 ml of [$^{35}$S]dATP-labeled DNA solution was added to the above suspension by extensive vortexing for about 1 minute and followed by freezing and thawing. Liposomes were separated from the non-entrapped [$^{35}$S]dATP by gel-filtration on a Sepharose 4B column equilibrated with PBS. About 50 µl calcein (about 10 mg/ml) was added into the solution in order to mark the liposomes during the separation. The specific activity of the entrapped DNA labeled [$^{35}$S] DATP was $2.5 \times 10^{10}$ cpm/µl measured by liquid scintillation counting.

Pieces of outbred white-haired-mouse skin (about 1×5×2 mm) derived from 1-5 week-old animals were harvested under a dissection microscope and then histocultured on collagen-gel-supported sponges as described in Example 1. Liposome interaction with the skin was initiated after about 24 hours of histoculture. Mouse skin histocultures were then incubated for about 44 hours with liposomes. As a control, a solution of naked-[$_{35}$S]DNA at the same concentration was used in the liposome preparation and was also incubated with skin histocultures.

The skin histocultures were washed with phosphate-buffered saline, pH 7.0, placed in histology capsules and fixed in 10% (v/v) formalin. The fixed skin cultures were then dehydrated, embedded in paraffin, sectioned and placed on slides by standard methods well known to those of skill in the histology art. The slides were deparaffinized, coated with Kodak NTB-2 emulsion, exposed for 5 days and developed. See, e.g. Freeman et al., Proc. Soc. Natl. Acad. Sci. USA 83:2694-2698, 1986; Hoffman et al., Proc. Soc. Acad. Sci. USA 86:2013-2017, 1989; and Li et al., Proc. Soc. Acad. Sci. USA 88:1908-1912, 1991. The developed slides were rinsed, stained with hematoxylin and eosin and examined using a Nikon or Olympus photomicroscope fitted with epi-illumination polarization.

Figure 4:
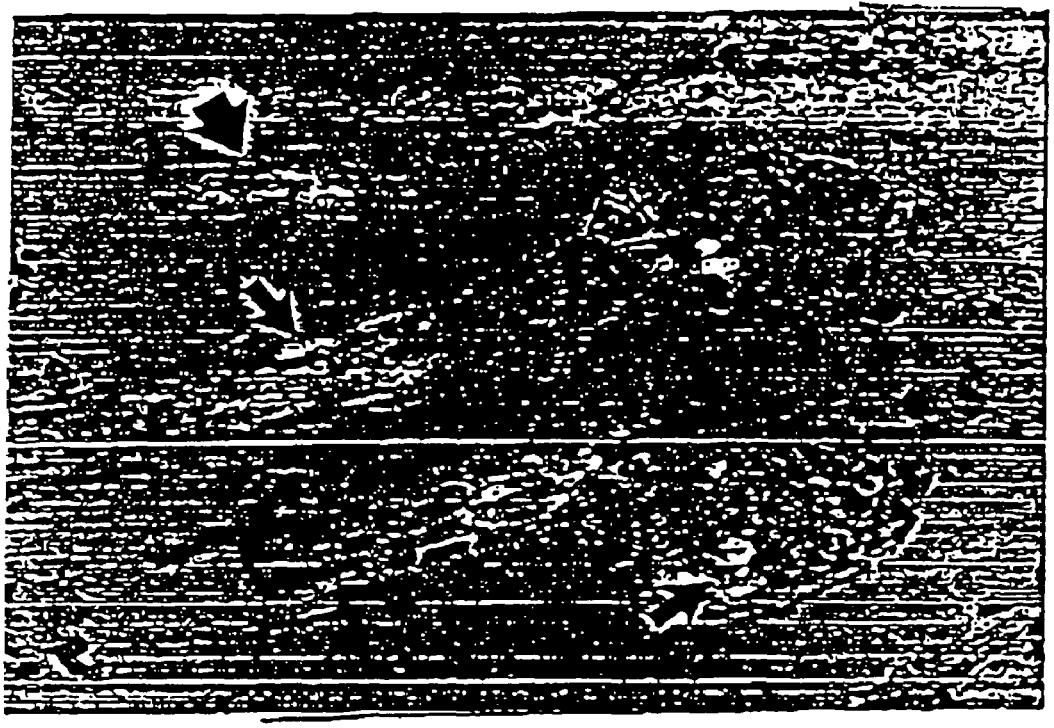
FIG. 4 is a histological autoradiogram of histocultured skin treated with liposomes entrapped with radioactive labeled high-molecular weight DNA showing the localization of DNA (arrows) in hair follicle cell membrane and cytoplasm, as described in Example 3.
Figure 5A:
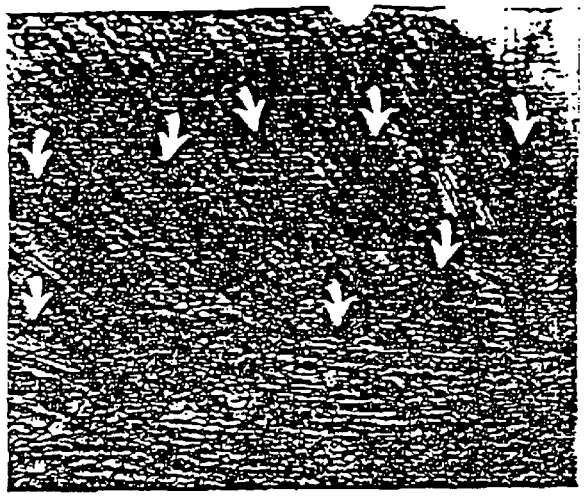
Figure 5C:
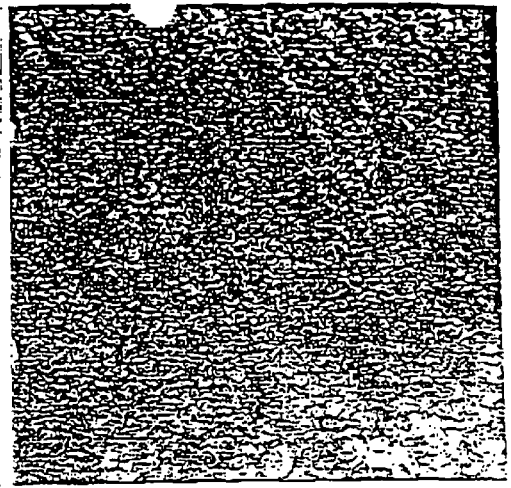
Figure 5B:
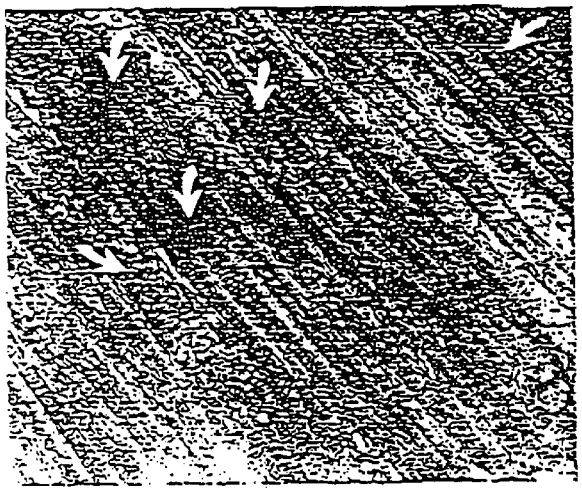
Figure 5D:

The histological autoradiogram of FIG. 4 shows [$^{35}$]DNA-labeled hair and follicle cells in the histocultured skin after the skin was incubated with the DNA liposomes for about 44 hours. High radioactive labeling by the [$^{35}$S]DNA in the cell membranes and cell cytoplasm as well as in the cell nucleus can be seen in FIG. 4, as pointed out by the arrows. This shows that the liposomes have delivered the DNA across the cell membrane and the DNA is transported through the cytoplasm to the nucleus.

When the histocultured skin was treated with naked-[$^{35}$S] DNA there were only a few radioactive labelled cells. For further comparison, the percent of labeled follicles per 20× field and percent of labeled cells per follicle in the areas of maximum labeling can be calculated from the autoradiogram of FIG. 4. The percent of labeled follicles per 20× field is found to be about 7 times higher for the liposome carrying labeled DNA compared to the naked labeled DNA, and the percent of labeled cells per follicle is at least 4 times higher for the liposome carried labeled DNA compared to the naked labeled DNA. For further comparison, we have calculated from the autoradiograms the percent of labeled follicles per 20× field and percent of labeled cells per follicle in the areas of maximum labeling. As can be seen in Table 1, both the percent of labeled follicles per 20× microscope field and percent of labeled cells per follicle in liposome-[$^{35}$S]DNA-treated skin histocultures are significantly higher than in naked-[$^{35}$S]DNA treated histocultures.

For further comparison, we have calculated from the autoradiograms the percent of labeled follicles per 20× field and percent of labeled cells per follicle in the areas of maximum labeling. As can be seen in Table 1, both the percent of labeled follicles per 20× microscope field and percent of labelled cells per follicle in liposome-[$^{35}$S] DNA-treated skin histocultures are significantly higher than in naked-[$^{35}$S] DNA treated histocultures.

TABLE 1

Liposome transfer of [$^{35}$S] DNA to hair follicles of histocultured skin.

|  | Lipo- [$^{35}$S] DNA | Naked- [$^{35}$S] DNA |  |
|---|---|---|---|
| Percent of labeled follicles per 20X field | 37.50 (6/16) | 5.41 (2/37) | p < 0.05 |
| Percent of labeled cells per follicle | 51.06 (24/47) | 9.30 (4/43) | p < 0.005 |

[$^{35}$S] DNA was entrapped in PC liposomes as described above. The liposomes were incubated with the skin histocultures described above. Naked [$^{35}$S] DNA was used as a control. Follicular [$^{35}$S] DNA was analyzed by histological autoradiography in the areas of maximum labeling.

This Example demonstrates that liposomes can specifically and efficiently target DNA into the hair follicles, and therefore establish that liposome encapsulated nucleic acids are useful reagents for targeting gene therapy to hair growth processes.

b. Delivery of Liposome-Entrapped Nucleic Acid Expressing the Human Tyrosinase Gene to a Cultured Cell Line Cloned human tyrosinase gene was transferred to tissue cultured cell lines using liposomes to demonstrate the efficiency of liposome-mediated delivery and expression of a tyrosinase gene.

To that end, liposomes were prepared by well known freezing and thawing methods. About 20 mg of phospholipid in a ratio of 5:3:2 of phosphatidylcholine (PC):cholesterol (Chol):phosphatidylethanolamine (PE) was rotary evaporated with a vacuum drier from a chloroform solution for 1 hour to form a thin film on the walls of a 5 ml round-bottomed flask for about 1 hour. The dried film phospholipid was suspended in 2 ml phosphate buffered saline solution at a pH of about 7.4 (PBS) in a vortex mixer and then sonicated with a Branson probe-type sonicator fitted with a microtip at power level 3 for about 8 minutes. Then 200 ug of the plasmid pRHOHT2 was entrapped in a liposome by addition of the plasmid to the sonicated suspension, sonication of the admixture in a water bath for 2 minutes, followed by freezing and thawing three times to form nucleic acid-containing liposome composition.

Plasmid pRHOHT2 was obtained from Dr. S. Shibahara and is described by Shibahara et al., *J. Biol. Chem.* 262: 12889-12892, 1987, and Takeda et al., *Biochem. Biophys. Res. Comm.* 162:984-990, 1989, and contains a full length human tyrosinase cDNA, including promoters for expression of tyrosinase in mammalian cells.

Human fibroblast FS-3 and mouse amelanotic K1735 cell lines were each pre-cultured in 60 mm culture dishes with Eagle's MEM medium containing 10% fetal bovine serum (FBS) and Dulbecco's Modified Eagle's medium containing 10 FBS, respectively, for 24 hours. Thereafter, the cultured cells were contacted with 0.5 ml of the tyrosinase gene-entrapped liposome composition in 1.5 ml of the respective culture medium per culture dish, and the contacted cells were maintained for 48 hours under culturing conditions. Thereafter, the cells were further cultured for 7 days (FS-3) or 3 days (K1735) with normal culture medium after aspiration of the liposome-containing medium.

The cells were then harvested by trypsin digestion and centrifuged at 800×g for 5 minutes to attach the cells to cytospin slides. As a control, 50 micrograms (ug) of naked plasmid in 0.5 ml medium was added to the two cell types in place of the 0.5 ml liposome preparation.

The expression of tyrosinase was evaluated by measuring dopa-oxidase reactions and immunohistochemical staining for tyrosinase in the treated cells.

To detect dopa oxidase activity, the cytospin slides were incubated with 1 mg/ml of L-dopa in PBS for 12 hours at 37 degrees C. as described by Kugelman et al., *J. Invest. Dermatol.* 37:73-76, 1961. Thereafter, the cytospin slides were counterstained with hematoxylin and eosin by established procedures, and the dopa oxidase-positive cells were identified and counted using a microscope.

To detect tyrosinase immunohistochemically, a Dako LSAB (labeled streptavidin-biotin) kit was used to stain tyrosinase-containing cells. The cytospin slides were fixed in acetone for 10 minutes, and then air-dried. Thereafter, serial incubations were then performed for 10 min each sequentially in hydrogen peroxide, blocking serum, a dilution (1:400) of primary antibody (anti-tyrosinase), linking antibody, peroxidase-conjugated streptavidin, and 3-amino-9-ehtylcarbazol substrate solution as described by the manufacturer of the kit (Dako, Carpinteria, Calif.). The primary antibody was rat anti-human tyrosinase monoclonal antibody TMH1 described by Tomita et al., *J. Invest. Dermatol.* 85:426-430, 1985, and Jimenez et al., *Proc. Natl. Acad. Sci. USA* 85:3830-3834, 1988. The linking antibody was a mixture of anti mouse and anti rat IgG conjugated to biotin, provided by the manufacturer (Dako). The treated cytospin slides were then lightly counterstained with Mayer's hematoxylin and mounted with liquid glycerol gelatin (Dako). A positive control was similarly prepared using a frozen section of human melanoma tissue. A negative control was prepared by replacing the primary antibody with PBS.

The results show tyrosinase expression in both FS-3 and K1735 liposome-treated cells, when detected by either dopa oxidase reaction or by immunohistochemical staining. The percent of cells expressing tyrosinase was approximately 52% of the total cells, by either assay method. The negative control cells were negative for both the oxidase assay and the immunohistochemical staining assay.

When compared to the calcium phosphate method for transfection of nucleic acid into cultured cells, it was observed that efficiency of transfer of a tyrosinase-gene expression plasmid into cells was about 50 times greater when liposomes were used in comparison to calcium phosphate.

These results demonstrate that liposomes are effective and efficient at delivering nucleic acid expression vectors into cells, and further that the liposomes can deliver expression vector plasmid which are subsequently able to express the encoded gene. Finally, the results demonstrate that the tyrosinase gene can be effectively introduced and expressed in mammalian cells.

c. Delivery and Expression of Beta-Galactosidase Gene in Hair Follicles of Histocultured Skin The bacterial gene Lac-Z encoding beta-galactosidase was delivered to histocultured skin samples in a liposome preparation to demonstrate selective delivery and expression in hair follicles. Plasmid pM-MuLV-SV-Lac-Z contains a mammalian promoter derived from the Moloney murine leukemia virus (M-MuLV) and the SV40 Virus (SV) which controls the expression of the beta-galactosidase gene (Lac-Z) capable of expression of beta-galactosidase in mammalian cells.

Liposomes were prepared as described in Example 3b, except that the phospholipids comprised PC, PE and cholesterol in a ratio of 5:2:3, and the ratio of plasmid DNA to phospholipid was 200 ug DNA per 20 mg total phospholipid.

White-haired mouse skin was histocultured as described in Example 1, except that the liposome composition was maintained in the culture medium for four days. Thereafter, the skin histoculture medium was changed to the same medium lacking liposomes and including the Lac-Z substrate X-gal, and the X-gal-containing medium was maintained under histoculturing conditions for 18 hours to allow any beta-galactosidase present in the histocultured skin sample to convert the X-gal to the typical visible blue dye. Control liposome delivery was conducted with naked plasmid DNA (pM-MuLV-SV-Lac-Z) using the same amount of DNA as with the liposome-entrapped plasmid composition.

Histocultured skin samples were then sectioned for histochemistry and evaluated using light microscopy at 125× and 250× magnification. The results are shown in FIGS. 5A-5D. The presence of expressed Lac-Z gene indicated by dark blue spots is only seen in FIGS. 5A and 5B which received liposome-entrapped plasmid; no dark spots are observed in FIGS. 5C and 5D. Furthermore, the dark spots are observed in the hair follicles and not significantly observable in the tissues adjacent to the hair follicles.

The results show that the Lac-Z gene was expressed in hair follicles and was not detectable in the other portions of the histocultured skin sample, indicating the selectivity of the liposome delivery method.

4. In Vivo Liposome-Mediated Delivery of Beneficial Compounds to Hair Follicles in Mice The present methods were used to deliver beneficial compounds to hair follicles in vivo by administration of a liposome composition of the present invention containing either melanin or calcein, or nucleic acid to mice.

a. Delivery of Melanin or Calcein to Hair Follicles in Mice

Liposomes were prepared essentially as described in Example 1. Twenty milligram (mg) of PC were rotary evaporated as described, and resuspended by sonication in 0.5 ml of PBS. Thereafter, 0.5 ml of either calcein (10 mg/ml) or melanin (10 mg/ml) solution, respectively, were added to sonicated PC liposome composition, and further sonicated for 6 minutes, followed by freeze-thawing three times. The resulting liposome composition was extruded through a 0.6-1.0 uM filter and separated from the non-entrapped calcein or melanin by gel filtration on a Sepharose 4B column eluted with PBS to form liposome-entrapped beneficial compound composition (calcein or melanin).

Two to 4 week-old pre-shaved outbred white-haired mice were used for in vivo topical liposome delivery of entrapped beneficial compound to hair follicles. A sample of about 250 microliters of the liposome composition entrapping calcein or melanin was applied directly to the dorsal skin on the mouse in an area of approximately 1.5 cm$^2$ using a sutured band-aid patch to immobilize the liposome composition onto the skin and to prevent evaporation. The liposome composition was re-applied every 1 hour for 6 hours, with the last application remaining for a total of 24 hours at which time the skin samples were taken by punch biopsy for analysis. For time course experiments, one mouse was used for each time period, with 6 punch biopsies taken from each mouse, at 0.5, 1, 2, 4, 6, 16 and 24 hours. Prior to punch biopsy, the skin was cleaned with an alcohol swab to eliminate any material remaining on the surface of the mouse's skin. For controls, the same amount of calcein or melanin was applied without liposome as with samples containing liposome-entrapped beneficial compound.

After liposome treatment, the skin samples were harvested and cut to very thin (5 mm) pieces of tissue sectioned along the vertical direction of the hair follicles, and subsequently observed by either light or fluorescent microscopy and photographed. For melanin-treated samples, the tissue sample was first counter-stained with BCECF-AM and propidium iodide (PI) for fluorescent microscopy, or prepared for histology and stained in paraffin sections using hematoxylin and eosin for light microscopy. For calcein-treated samples, the tissue sample was first counter-stained with propidium iodide (PI) for fluorescent microscopy.

Skin samples containing calcein were also analyzed by spectrofluorimetry to determine the effective concentration of a delivered beneficial compound into a selected tissue. To that end, three samples each containing two pieces of a 2-mm punch biopsy of skin for each time point were put into 2 ml of PBS and sonicated in the water bath sonicator for 2 min. The sonicated sample was then centrifuged for 10 minutes in a microcentrifuge at 14,000×g, and the resulting supernatant was measured by spectrofluorimetry at an excitation wavelength of 496 nm and an emission wavelength of 517 nm for detecting calcein. The concentration of calcein delivered into the skin tissue was determined from the spectrofluorometric readings by comparison to a standard curve.

Figure 6C:
Figure 6B:
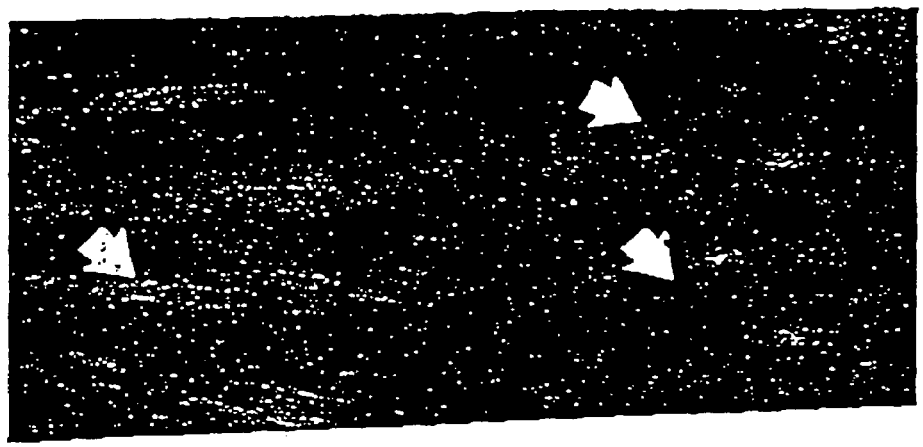
Figure 6A:
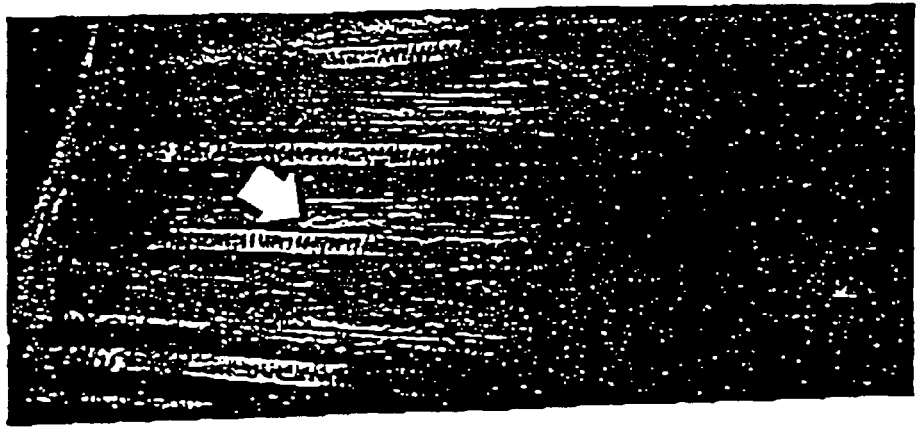

FIGS. 6A-6C show the results of delivery of calcein using liposome-entrapped calcein (FIGS. 6A and 6B) and naked calcein (FIG. 6C) after 20 hours. Notice that the liposome-mediated delivery has allowed the calcein to penetrate deep into the hair follicles and shafts, whereas control calcein was trapped in the stratum corneum and did not enter the hair shafts or follicles.

Time course analysis of effectiveness of liposome-entrapped calcein-mediated delivery showed that by 24 hours 22.15 nanograms (ng) per mm$^2$ of calcein was observed delivered in the hair follicles, whereas only about 1.4 ng/mm$^2$ of naked calcein was observed delivered after 24 hours, and this amount did not increase with time.

Figure 7A:
Figure 7B:
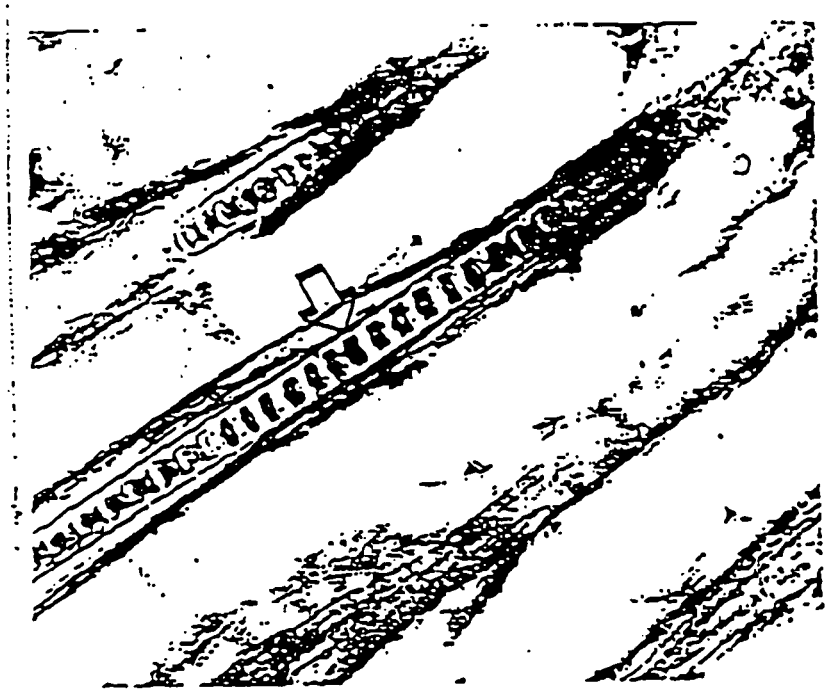
Figure 7C:
Figure 8A:
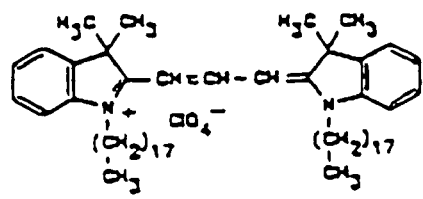
FIGS. 8A-8F shows the chemical structure of the cationic phospholipids D282, D378, D383, D3886, D3897 and D3899, respectively.
Figure 8B:
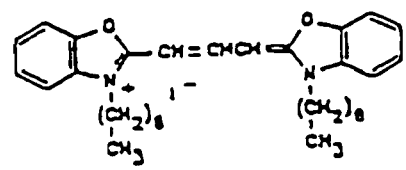
Figure 8C:
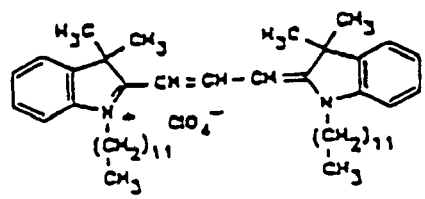
Figure 8D:
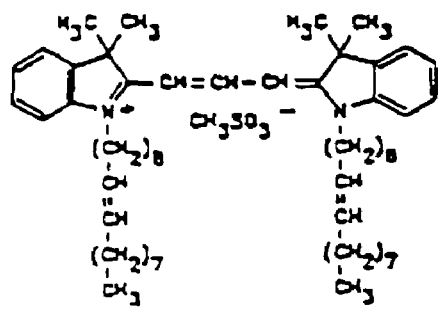
Figure 8E:
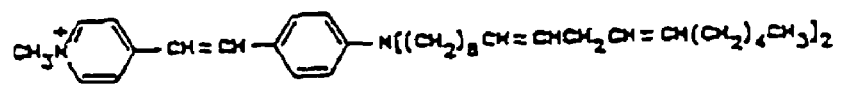
Figure 8F:
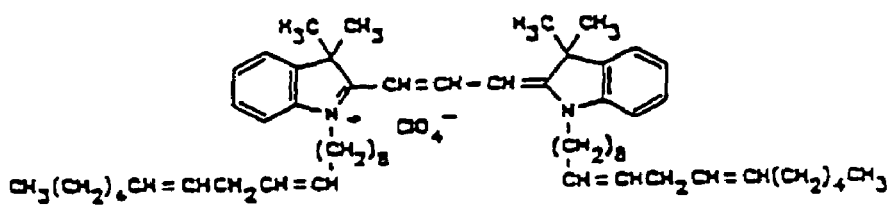

FIGS. 7A-7C illustrate the results in which melanin has been delivered using liposome-entrapped compound after 24 hours of treatment. FIGS. 7A and 7B show the melanin delivered into the hair shafts in a pattern that illustrates that the delivered melanin forms the exact pattern of naturally melanized hair shafts. FIG. 7C shows the melanin delivered into the hair follicle cells. Therefore, these results demonstrate that topical in vivo administration of liposome resulted in delivery of melanin to both the hair follicle and hair shaft.

Skin samples containing melanin were also analyzed by is spectrophotometry to determine the effective concentration of a delivered beneficial compound into a selected tissue. To that end, three samples each containing two pieces of a 2-mm punch biopsy of skin for each time point were put into 2 ml of PBS and sonicated in the water bath sonicator for 2 min. The sonicated sample was then centrifuged for 10 minutes in a microcentrifuge at 14,000×g, and the resulting supernatant was measured by spectrophotometry at an absorption wavelength of 300 nm for detecting absorption by melanin. The concentration of melanin delivered into the skin tissue was determined from the spectrophotometric readings by comparison to a standard curve.

Readings from the skin samples in the time course study showed that liposome-entrapped melanin was delivered specifically to the hair follicles after 16 hours to a level of about 19.0 ug/mm$^2$ whereas less than 2.0 ug/mm$^2$ of melanin was delivered in the same time period using non-entrapped melanin.

The above results indicate that the liposome-targeted melanin or calcein were selectively delivered to the hair follicle and hair shafts within the follicle, but non-entrapped compound was not delivered to the hair follicle, and instead was restricted to the skin surface, particularly the stratum corneum. Therefore, the liposome-mediated delivery of beneficial compounds is seen to be effective at specific delivery to hair follicles and hair shafts in a living animal, demonstrating in vivo efficacy of the liposome-mediated delivery methods described herein.

As a further control plasma calcein concentrations were also measured by taking blood samples from the lateral tail vein of mice during the course of administration of liposome-entrapped calcein at 0.5, 1, 2, 4, 6, and 24 hours after topical administration. The harvested blood was transferred to a serum separator tube (Vacutainer, Becton Dickinson), and spun at 2000×g for 10 min to isolate plasma. Thereafter, calcein was measured by spectrofluorimetry at an excitation wavelength of 496 nm and an emission wavelength of 517 nm for detecting calcein. The concentration of calcein in the plasma was determined from the spectrofluorometric readings by comparison to a standard curve. Over a 24 hour time period, no detectable calcein entered the blood circulation. This is an important observation as it indicates that a beneficial compound, when administered by the present liposome-mediated methods, can be selectively targeted to the hair follicle and hair shaft without entry into the systemic circulation where it may exert undesirable side effects, and that safe follicle/shaft delivery is possible.

b. Delivery and Expression of Beta-Galactosidase Gene in Hair Follicles of Mice

1. Purification of Lac-Z DNA

A recombinant retrovirus containing the Lac-Z gene (pM-MuLV-SV-LacZ) was obtained from Dr. Joshua R. Sanes (Washington University, St. Louis) (Sanes et al., *EMBO J.* 5:3133-42, 1986). Other expression vectors comprising the Lac-Z gene may also be employed, such as pCH110, which contains the SV40 early promoter (Pharmacia Biotech). The plasmid Lac-Z was transformed to HB101 *E. coli* competent cells (Promega) by standard methods. The purification of plasmid Lac-Z DNA was obtained by using the Promega Wizards Megaprep DNA purification system.

2. Preparation of Lac-Z-liposomes

A total of 20 mg of lipid in a ratio of 5:3:2 of phosphatidylcholine (PC): cholesterol (Chol): phosphatidylethanolamine (PE) were rotary evaporated for 1 hour with a vacuum drier from a chloroform solution to form a thin film on the wall of a 5 ml round-bottomed flask. The dried thin film lipid was suspended in 0.6 ml Tris-EDTA (TE) buffer containing approximately 1 mg of Lac-Z DNA on a vortex mixer. The Lac-Z DNA was entrapped by sonication in a compact water bath sonicator for 20 minutes, followed by freezing (at −70° C.) and thawing (at room temperature) three times.

3. Topical Application of Lac-Z-Liposomes

Pre-shaved 5-6 week old Balb-c mice were used for the hair follicle gene therapy experiment. The skin area for application of liposome-Lac-Z was pre-hydrated with phosphate-buffered saline (PBS) for 10-30 minutes. 50 μl of liposome-Lac-Z formulation were directly put on the skin area with reapplication after one hour. Untreated mice and mice treated with naked Lac-Z DNA mice were used as controls. The skin was carefully cleaned by 70% isopropyl alcohol before harvest for X-gal staining 3 days after application of the liposome-Lac-Z formulation.

4. Detection of Lac-Z DNA Expression by X-Gal Staining.

The harvested skin samples were immediately put into a MEM wash medium containing a combination of antibiotics at 4° C. for 1 hour and then fixed in 2% (v/v) formaldehyde-0.2% (v/v) glutaraldehyde in PBS for 30 minutes at 4° C. The tissues were then rinsed with PBS three times and incubated in the X-gal staining solution containing 1 mg/ml X-gal, 5 mM potassium ferricyanide, 5 mM potassium ferrocyanide, and 2 mM $MgCl_2$ in PBS, at 37° C. for 18 hours. Skin tissues were processed for paraffin sectioning by standard histological procedures and photographed under light microscopy after counter-staining with 0.1% nuclear fast red.

Figure 14:
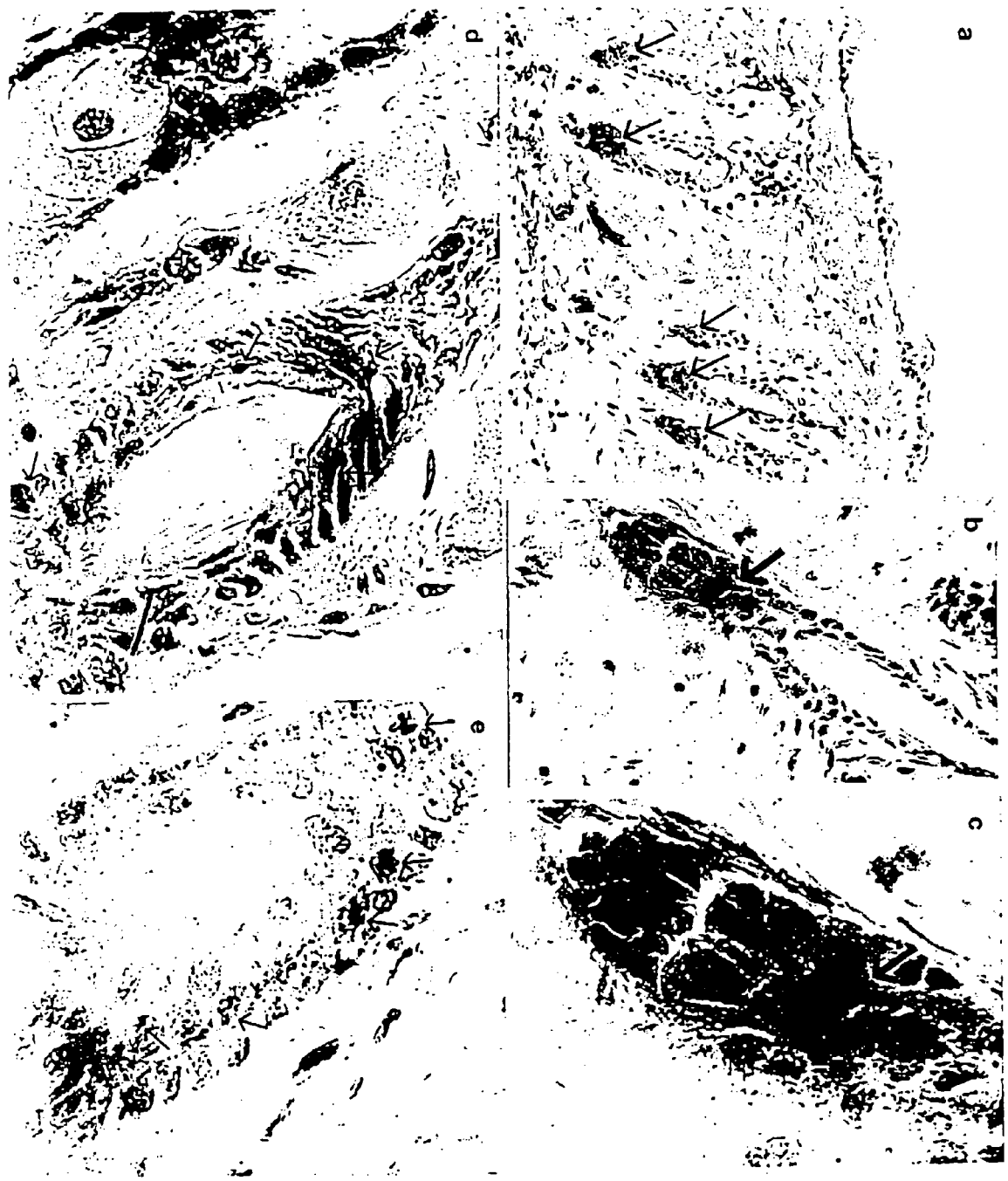
FIGS. 14A-E are light microscopic images of β-galactosidase expression in mouse hair follicle cells after topical application of liposome-entrapped Lac-Z. Expression of β-galactosidase results in blue staining of X-gal substrate in hair follicle bulbs (14A-C) and in the bulge area below the opening of the sebaceous gland (14D&E) as described in Example 4. Magnification 200× (A), 400× (B), 1000× (c,d,e).

FIG. 14 illustrates the results of topical application of liposome Lac-Z to mice. Blue stain indicates gene activity in the hair follicles after staining with the X-gal substrate. Note the selective delivery of the active gene to the hair matrix cells in the follicle bulbs (a-c) and also to what may be follicle stem cells in the bulge area (d & e). Note the high frequency of transfection of Lac-Z gene in the hair follicles (a) and also total lack of gene activity outside the hair follicle (a & b). Nuclear fast red counter-staining. Light Microscopy. Magnification 200× (a), 400× (b), 1000× (c,d,e).

FIG. 14 shows that after topical application of liposome-Lac-Z, the expression of the Lac-Z gene, indicated by blue staining of the X-gal substrate, was in the hair-forming hair matrix cells in the hair follicle bulbs (FIG. 14*a-c*) and in the bulge area (FIG. 14*d* & *e*) below the opening of the sebaceous gland, which is thought to contain the follicle stem cells (Cotsralelis et al., *Cell* 61:1329-1337, 1990). The transfection frequency was high since many follicles are stained by X-gal (FIG. 14*a*). No other cells were transfected with Lac-Z outside the follicle in the dermis or epidermis (FIG. 14*a*). FIG. 14*b* demonstrates the expression of the Lac-Z gene in the hair matrix cells. The extensive Lac-Z expression in the hair matrix cells can be seen very clearly at high magnification (FIG. 14*c*). The transfection of what may be follicle stem cells can be seen in FIG. 14*d* & *e*. The introduction of active genes in stem cells is important for long-term modification of the hair follicle. Topical application of the naked Lac-Z gene did not result in gene transfer and no Lac-Z staining can be seen in follicles in animals not treated with liposome-Lac-Z (data not shown). These results demonstrate that genes can be selectively targeted to the most important cells of the hair follicle by liposomes. The targeting of the reporter gene to the hair follicle cells is the most selective targeting of a gene observed thus far in vivo (Caplen et al., *Nature Med.* 1:39-46, 1995). The high hair-follicle selectivity of gene targeting by topical liposome application suggests the feasibility of gene targeting of hair matrix cells and possibly follicle stem cells to restore hair color such as with the tyrosinase gene (Shibahara et al., *J. Exp. Med.* 156:403-405, 1988; Tanaka et al., *Development* 108:223-227, 1990) and with genes to restore hair growth. The high selectivity of topical liposome gene targeting is also important for safety and cosmetic reasons.

5. Screening for Compounds Which Increase or Decrease Chemotheracy-Induced Alopecia a. In Vitro Model of Chemotherapy-Induced Alopecia 5-day old Sprague-Dawley rat skin tissues (4 mm size punch) are explanted on the collagen-containing gels and histocultured for 3 days. The skin histocultures are then treated with melphalan (40 ug/ml)+doxorubicin (1.16 ug/ml) for 4 days. To screen for compounds that prevent alopecia in vitro, the skin histocultures are pretreated with liposomes containing the compound as described in Example 1, (100 μg/ml, 1 mM β-ME) for 2 days after an initial 24 hours histoculture. Liposome-compound treatment is maintained during chemotherapy for 4 days of histoculture. Four pieces of skin tissue are used in each group. Control is skin histoculture without pre-treatment and chemotherapy. The effect of chemotherapy on hair loss and prevention by the compound in histocultured skin was determined by dissection microscopy.

Cell cycle inhibitors are an example of compounds that may be used to prevent chemotherapy-induced alopecia. An example of a cell cycle inhibitor, p21, has been tested by the present inventors and has been found to prevent chemotherapy-induced alopecia. An expression vector comprising a nucleic acid molecule coding for p21 (Noda et al., *Expt'l Cell Res.* 211, 1994) was entrapped in a liposome composition according to the methods of the present invention. The liposome formulation contained a ratio of phosphatidylcholine:cholesterol:phosphatidylethanolamine of 5:3:2, however, any of the liposome compositions of the present invention, may be used. The ratio of lipid: p21-expression vector was approximately 10:1, this ratio may vary, as described herein.

The p21/liposome composition was used to pretreat the skin histoculture as described in this Example. The skin histoculture was then treated with the chemotherapeutic drugs and p21/liposome treatment continued as described herein. The pretreatment with p21/liposomes was found to prevent almost completely the chemotherapy induced alopecia in the skin histoculture when compared to the control skin histoculture which was treated with the chemotherapeutic drugs but not with the p21 liposome composition.

b. In Vivo Model of Chemotherapy-Induced Alopecia 8-day old Sprague-Dawley rats are treated topically with liposome compositions as described in Example 1 containing a compound such as p21 to be screened for its effect on chemotherapy-induced alopecia. The liposome composition is provided at a concentration of 100 µg/ml in 1 mM β-mercaptoethanol, for 2 days. In a control group, the rats do not receive liposome pretreatment. The rats are then treated with cyclophosphamide, CTX (35 mg/kg, ip once) with the combination of CTX (25 mg/kg)+doxorubicin, DOX (2.5 mg/kg), ip once per day for 3 days, respectively. One rat pup without chemotherapy was used as control. Alopecia was noted at day-7 after chemotherapy.

In rats that received chemotherapy, alopecia can be seen in both the CTX-treated and CTX+DOX-treated rat pups. No other toxic effects were noted.

CTX and doxorubicin can induce alopecia in rat pups by day-7 without other noticeable toxic effects. Rats that received the liposome composition pretreatment may be compared to the control rats to determine whether the screened compound had an effect on chemotherapy-induced alopecia.

Although the present invention has now been described in terms of certain preferred embodiments, and exemplified with respect thereto, one skilled in the art will readily appreciate that various modifications, changes, omissions and substitutions may be made without departing from the spirit thereof.

One skilled in the art will readily appreciate that the present invention is well adapted to carry out the objects and obtain the ends and advantages mentioned as well as those inherent therein. The liposome compositions, along with the methods, procedures and treatment described herein are presently representative of preferred embodiments that are exemplary and not intended as limitations on the scope of the invention. Changes therein and other uses will occur to those skilled in the art which are encompassed within the spirit of the invention or defined by this scope with the claims.

It will be readily apparent to one skilled in the art that varying substitutions and modifications may be made to the invention disclosed herein within departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

What is claimed is:

1. A method of directly and selectively delivering a beneficial compound to hair follicles of a mammal comprising the step of applying a liposome composition topically to skin areas of a mammal having a plurality of hair follicles,
    said liposome composition comprising a liposome containing an effective amount of at least one selected beneficial compound,
    wherein said composition has been treated so as to remove any unencapsulated compound and wherein said compound is delivered into the hair follicle directly and selectively and not delivered into the circulation or into cells that are not hair follicle cells,
    whereby said beneficial compound is transmitted to said hair follicles and enters into said hair follicles.

2. The method of claim 1 wherein said compound comprises melanin.

3. The method of claim 1 wherein said compound comprises hair dye.

* * * * *